(12) United States Patent
Nelson

(10) Patent No.: US 9,434,925 B2
(45) Date of Patent: Sep. 6, 2016

(54) GENETICALLY MODIFIED MESENCHYMAL STEM CELL THAT EXPRESS AN EXOGENOUS CYTOTOXIC PROTEIN

(75) Inventor: Peter Nelson, Munich (DE)

(73) Assignee: APCETH GMBH & CO. KG, Munich (DE)

(*) Notice: Subject to any disclaimer, the term of this patent is extended or adjusted under 35 U.S.C. 154(b) by 503 days.

(21) Appl. No.: 13/264,084

(22) PCT Filed: Apr. 13, 2010

(86) PCT No.: PCT/EP2010/054844
§ 371 (c)(1),
(2), (4) Date: Dec. 23, 2011

(87) PCT Pub. No.: WO2010/119039
PCT Pub. Date: Oct. 21, 2010

(65) Prior Publication Data
US 2012/0087901 A1 Apr. 12, 2012

Related U.S. Application Data

(60) Provisional application No. 61/168,787, filed on Apr. 13, 2009.

(51) Int. Cl.
A61K 48/00 (2006.01)
C12N 5/0775 (2010.01)
A61K 35/12 (2015.01)

(52) U.S. Cl.
CPC ....... *C12N 5/0663* (2013.01); *A61K 2035/124* (2013.01); *C12N 2510/00* (2013.01)

(58) Field of Classification Search
USPC ................................................... 424/93.21
See application file for complete search history.

(56) References Cited

U.S. PATENT DOCUMENTS

| 2003/0165579 A1* | 9/2003 | Lin et al. ............... 424/725 |
| 2004/0053389 A1* | 3/2004 | Rowe ...................... 435/196 |
| 2007/0148191 A1* | 6/2007 | Krenn et al. .......... 424/277.1 |
| 2008/0241115 A1* | 10/2008 | Suh et al. ............. 424/93.21 |

FOREIGN PATENT DOCUMENTS

WO WO2008/150368 12/2008

OTHER PUBLICATIONS

Miletic (Gene Therapy Jul. 2007, vol. 15, p. 1373-1381).*
Pfeifer (Annu. Rev. Genomics. Hum. Genet. 2001, vol. 2, p. 177-211).*
Johnson-Saliba (Curr. Drug. Targets, 2001, vol. 2, p. 371-399).*
Shoji (Current Pharmaceutical Design, 2004, vol. 10, p. 785-796).*
Miller (1995, FASEB J., vol. 9, pp. 190-199).*
Deonarain (1998, Expert Opin. Ther. Pat., vol. 8, pp. 53-69).*
Verma (Sep. 1997, Nature, vol. 389, pp. 239-242).*
Crystal (1995, Science, vol. 270, p. 404-410).*
Miletic (Molecular Therapy, vol. 15, No. 7, Jul. 2007, p. 1373-1381).*
Vilalta (Gene Therapy, vol. 16, No. 4, Apr. 2009, Online publication Dec. 18, 2008, p. 547-557).*
Karnoub "Mesenchymal stem cells within tumour stroma promote breast cancer metastasis." Nature, vol. 449, No. 7162, Oct. 4, 2007, pp. 557-563.*
Zischek (Annals of Surg., Nov. 2009, vol. 250, No. 5, p. 747-753).*
Loebinger (Thorax, Apr. 2010, vol. 65, No. 4, p. 362-369).*
Von Luettichau (Cytokine, 1996, vol. 8, No. 1, p. 89-98.*
Rivella (J. Virol., 2000, vol. 74, p. 4679-4687.*
Andoh, A. et al.: "Cytokine Regulation of Chemokine (IL-8, MCP-1, and RANTES) Gene Expression in Human Pancreatic Periacinar Myofibroblasts" Gastroenterology 2000; 119(1): pp. 211-219.
Korc, M.: "Pancreatic Cancer-Associated Stroma Production" Am J Surg 2007; 194(4 Suppl): pp. 84-86.
Liyanage, U. et al.: "Increased Prevalence of Regulatory T Cells (Treg) is Induced by Pancreas Adenocarcinoma" J Immunother 2006; 29(4):pp. 416-424.
Miletic, H., et al.: "Selective Transduction of Malignant Glioma by Lentiviral Vectors Pseudotyped with Lymphocytic Choromeningitis Virus Glycoproteins" Hum Gene Ther 15: 1091-1100. Hum Gene Ther 15: pp. 1091-1100.
Morikane, K. et al.: "Organ-Specific Pancreatic Tumor Growth Properties and Tumor Immunity" Cancer Immunol Immunother 1999;47(5): pp. 287-296.
Nelson, P. et al.: "Gene Expression of RANTES" Methods Enzymol 1997; 287: pp. 148-162.
Nelson, P. et al.: "Genomic Organization and Transcriptional Regulation of the RANTES Chemokine Gene" J Immunol 1993; 151(5): pp. 2601-2612.
Segerer, S. et al.: "CXCR3 is involved in Tubulointerstitial Injury in Human Glomerulonephritis" Am J Pathol 2004; 164(2): pp. 635-649.
Soria, G. et al.: "The Inflammatory Chemokines CCL2 and CCL5 in Breast Cancer" Cancer Lett 2008; 267(2): pp. 271-285.
Von Luettichau, I. et al.: "RANTES Chemokine Expression in Diseased and Normal Human Tissues" Cytokine 1996; 8(1):89-98.
Von Luttichau, I. et al.: "Human Adult CD34-Progenitor Cells Functionally Express the Chemokine Receptors CCR1, CCR4, CCR7, CXCR5, and CCR10 but not CXCR4" Stem Cells Dev 2005; 14(3): pp. 329-336.
Zipori D., The Mesenchyme in Cancer Therapy as a Target Tumor Component, Effector Cell Modality and Cytokine Expression Vehicle. Cancer Metastasis Rev 2006; 25(3):459-67.

(Continued)

*Primary Examiner* — Michael Wilson
(74) *Attorney, Agent, or Firm* — Knobbe, Martens, Olson & Bear, LLP

(57) ABSTRACT

This invention provides a method for treating a subject afflicted with a tumor using genetically modified mesenchymal stem cells, wherein each genetically modified mesenchymal stem cell contains an exogenous nucleic acid comprising (i) a cytotoxic protein-encoding region operably linked to (ii) a promoter or promoter/enhancer combination, whereby the cytotoxic protein is selectively expressed when the genetically modified mesenchymal stem cells come into proximity with the tumor's stromal tissue. This invention further provides genetically modified mesenchymal stem cells for use in this method.

30 Claims, 11 Drawing Sheets

(56) References Cited

OTHER PUBLICATIONS

Duell, E. et al.: "Inflammation, Genetic Polymorphisms in Proinflammatory Genes TNF-A, RANTES, and CCR5, and Risk of Pancreatic Adenocarcinoma" Cancer Epidemiol Biomarkers Prev 2006; 15(4): pp. 726-731.

Farrow, B. et al.: "Inflammatory Mechanisms Contributing to Pancreatic Cancer Development" Ann Surg 2004; 239(6):763-9; discussion 769-71.

Fischer, M. et al.: "Expression of CCL5/RANTES by Hodgkin and Reed-Sternberg Cells and its Possible Role in the Recruitment of Mast Cells into Lymphomatous Tissue" Int J Cancer 2003; 107(2): pp. 197-201.

Fritz, V. et al.: "Mesenchymal Stem Cells: an Emerging Tool for Cancer Targeting and Therapy" Curr Stem Cell Res Ther 2008; 3(1):32-42. Curr Stem Cell Res Ther 2008; 3(1): pp. 32-42.

Golumbek, P. et al.: "Herpes Simplex-1Virus Thymidine Kinase Gene is Unable to Completely Eliminate Live, Nonimmunogenic Tumor Cell Vaccines" J Immunother 1992; 12(4):224-30.

Miletic, H. et al.: "Bystander killing of malignant glioma by bone marrow-derived tumor infiltrating progenitor cells expressing a suicide gene." Molecular Therapy: The Journal of the American Society of Gene Therapy Jul. 2007LNKD—Pubmed:17457322, vol. 15, No. 7, Jul. 2007, pp. 1373-1381. XP002589918.

Vilalta, M. et al., "Human adipose tissue-derived mesenchymal stromal cells as vehicles for tumor bystander effect: a model based on bioluminescence imaging." Gene Therapy Apr. 2009 LNKD—PUBMED: 19092860, vol. 16, No. 4, Dec. 18, 2008, pp. 547-557, XP002589919.

Karnoub A., et al., "Mesenchymal stem cells within tumor stroma promote breast cancer metastasis." Nature Oct. 4, 2007 LNKD—PUBMED: 17914389, vol. 449, No. 7162, Oct. 4, 2007, pp. 557-563, XP992578829.

Zischek, C., et al: "Targeting tumor stroma using engineered mesenchymal stem cells reduces the growth of pancreatic carcinoma." Annals of Surgery Nov. 2009 LNKD—PUBMED: 19826249, vol. 250, No. 5, Nov. 2009, pp. 747-753, XP008123905.

Loebinger, M., et al., "Stem cells as vectors for antitumor therapy." Thorax Apr. 2010 LNKD—PUBMED: 20388765, vol. 65, No. 4, Apr. 2010, pp. 362-369, XP008123904.

Karnoub, Antoine E., et al., "Chemokine Networks and Breast Cancer Metastasis", Breast Disease 26 (2006-2007) 75-85, IOS Press.

Corbett, T.H., et al., "Induction and Chemotherapeutic Response of Two Transplantable Ductal Adenocarcinomas of the Pancreas in C57BL/6 Mice", Cancer Research 44, 717-726, Feb. 1984.

Kanehira, M., et al., "Oncogenic Role of MPHOSPH1, a Cancer-Testis Antigen Specific to Human Bladder Cancer", Cancer Res 2007; 67: (7). Apr. 1, 2007.

Orimo, A., et al., "Stromal Fibroblasts in Cancer, A Novel Tumor-Promoting Cell Type", Cell Cycle 5-15, 1597-1601, Aug. 1, 2006); 2006 Landes Bioscience.

Conrad, C., et al., "Multipotent Mesenchtnak Stem Cells Acquire a Lymphendothelial Phenotype and Enhance Lymphatic Regeneration in Vivo", DOI:10.1161/Circulationaha.108.793208.

Ahmed, F., et al., "Tumor Stroma as a Target in Cancer", Current Cancer Drug Targets, 2008, 8, 447-453.

Conrad, C., et al., "Genetically Engineered Stem Cells for Therapeutic Gene Delivery", Current Gene Therapy, 2007, 7, 249-260.

Kiaris, H., et al., "Regulation of Tumor-Stromal Fibroblast Interactions: Implication in Anticancer Therapy", Current Medicinal Chemistry, 2008, 15, 3062-3067.

Fesselle, S., et al., "Molecular and in silico characterization of a promoter module and C/EBP element that mediate LPS-induced RANTES/CCL5 expression in monocytic cells", The FASEB Journal, vol. 15 Mar. 2001.

Werner, T., et al., "Computer modeling of promoter organization as a tool to study transcriptional coregulation", The FASEB Journal, vol. 17 Jul. 2003.

Treschow, A., et a., "OuaSelect, a novel ouabain-resistant human marketer gene that allows efficient cell selection within 48 h", Gene Therapy (2007) 14, 1564-1572.

West, A., et al., "Insulator: many functions, many mechanisms", Genes and Development 16:271-288 © 2002 by Cold Spring Harbor Laboratory Press ISSN 0890-9369/02.

Inman, G., et al., "Stoichiometry of Active Smad-Transcription Factor Complexes on DNA", The Journal of Biological Chemistry © 2002 by The American Society for Biochemistry and Molecular Biology, Inc., vol. 277, No. 52, Issue of Dec. 27, pp. 51008-51016, 2002.

Kumar, D., et al., "JNK MAPK Pathway Regulates Constitutive Transcription of CCL5 by Human NK Cells through SP1", © 2009 by The American Association of Immunologists, Inc. 0022-1767/09.

Möller, C., et al., "Expression and Function of chemokine receptors in human multiple myeloma", Leukemia (2003) 17, 203-210.

Fehse, B., et al., "CD34 Splice Variant: An Attractive Marker for Selection of Gene-Modified Cells", Molecular Therapy vol. 1, No. 5, May 2000.

Bergoglio, V., "Safe selection of Genetically Manipulated Human Primary Keratinocytes with Very High Growth Potential Using CD 24", www.moleculartherapy.org vol. 15 No. 12, 2186-2193 Dec. 2007.

Zychlinski, D., et al., "Physiological Promoters Reduce the Genotoxic Risk of Integrating Gene Vectors", www.moleculartherapy.or vol. 16 No. 4, 718-725 Apr. 2008.

Bexell, D., et al., Bone Marrow Multipotent Mesenchymal Stroma Cells Act as Pericyte-like Migratory Vehicles in Experimental Gliomas, Molecular Therapy vol. 17 No. 1, 183-190 Jan. 2009.

Hu, W., et al., "Design of Retroviral Vectors and Helper Cells for Gene Therapy", Pharmacological Reviews vol. 52, No. 4 43/865931.

Huber, B., et al., "Metabolism of 5-fluorocytosine to 5-fluorouracil in human colorectal tumor cells transduced with the cytosine deaminase gene: Significant antitumor effects when only a small percentage of tumor cells express cytosine deaminase", Proc. Natl. Acad. Sci. USA vol. 91, pp. 8302-8306, Aug. 1994.

Wu, S., et al., "piggyback is a flexiable and highly active transposon as compared to Sleeping Beauty, Tol2, and Mos1 in mammalian cells", www.pnas.org/cgi/doi/10.1073/pnas.0606979103.

Wei, Q., et al., "Section of Genetically Modified Chicken Blastodermal Cells by Magnetic-Activated Cell Sorting", Department of Medical Sciences, University of Guelph, Guelph, Ontario, Canada; and +Origen Therapeutics, 14350 Rollins Road, Burlingame, California 94010.

Horwitz, EM., et al., Position Paper "Clarification of the nomenclature for MSC: The International Society for Cellular Therapy position statement", International Society for Cellular Therapy, Cytotherapy (2005) vol. 7, No. 5, 393-395.

Stoff-Khalili et al., Mesenchymal stem cells as a vehicle for targeted delivery of CRAds to lung metastases of breast carcinoma, *Breast Cancer Res Treat*, vol. 150, pp. 157-167 (2007).

Balkwill, "Smoldering and polarized inflammation in the initiation and promotion of malignant disease," *Cancer Cell*, vol. 7, pp. 211-217 (2005).

Conrad et al., "GATA transcription in a small rhodamine 123(low)CD34(+) subpopulation of a peripheral blood-derived CD34(−)CD105(+) mesenchymal cell line," *Experimental Hematology*, vol. 30, No. 8, pp. 887-895 (2002).

Deeg et al., "A Guide to Bone Marrow Transplantation," Springer-Verlag Berlin Heidelberg, 12 pages (1992).

Dinunzio et al., "Transduction of human hematopoietic stem cells by lentiviral vectors pseudotyped with the RD114-TR chimeric envelope glycoprotein," *Human Gene Therapy*, vol. 18, pp. 811-820 (2007).

Fessele et al., "Regulatory context is a crucial part of gene function," *Trends in Genetics*, vol. 18, No. 2, pp. 60-63 (2002).

Gennaro, "Remington: The Science and Practice of Pharmacy," $20^{th}$ Ed., Lippincott Williams & Wilkins, p. 808 (2000).

Izsvak et al., "Sleeping Beauty, a wide host-range transposon vector for genetic transformation in vertebrates," *Journal of Molecular Biology*, vol. 302, pp. 93-102 (2000).

(56) References Cited

OTHER PUBLICATIONS

Khoury et al., "Inflammation-inducible anti-TNF gene expression mediated by intra-articular injection of serotype 5 adeno-associated virus reduces arthritis," *The Journal of Gene Medicine*, vol. 9, pp. 596-604 (2007).

Koka et al., "Regulation of the Production of the RANTES Chemokine by Endothelial Cells," *The Journal of Immunology*, vol. 154, pp. 1870-1878 (1995).

Li et al., "Tumor Microenvironment: The Role of the Tumor Stroma in Cancer," *Journal of Cellular Biochemistry*, vol. 101, pp. 805-815 (2007).

Niess et al., "Selective Targeting of Genetically Engineered Mesenchymal Stem Cells to Tumor Stroma Microenvironments Using Tissue-Specific Suicide Gene Expression Suppresses Growth of Hepatocelluriar Carcinoma," *Annals of Surgery*, vol. 254, No. 5, pp. 767-775 (2011).

Niwa et al. "Efficient selection for high-expression transfectants with a novel eukaryotic vector,", *Gene*, vol. 108, pp. 193-199 (1991).

Stitz et al., "Lentiviral vectors pseudotyped with envelope glycoproteins derived from gibbon ape leukemia virus and murine leukemia virus 10A1," *Virology*, vol. 273, pp. 16-20 (2000).

Kalevi J. Pulkkanen et al. Molecular Therapy vol. 12, No. 4, Oct. 2005, Copyright © The American Society of Gene Therapy, "Gene Therapy for Malignant Glioma: Current Clinical Status" pp. 585-598.

Hirofumi Hamada et al., "Mesenchymal stem cells (MSC) as therapeutic cytoreagents for gene therapy" Cancer Sci. Mar. 2005, vol. 96, No. 3, pp. 149-156.

Sabine Fessele et al. The FASEB Journal express article 10.1096/fj.00-0459fje. Published online Jan. 5, 2001. "Molecular and in silico characterization of a promoter module and C/EBP element that mediate LPS-induced RANTES/CCL5 expression in monocytic cells" pp. 1-19.

Jae Heon Kim et al.; Hindawi Publishing Corporation BioMed Research International vol. 2014, Article ID 549136, 8 pgs, http://dx.doi.org/10.1155/2014/549136 "Stem Cell Based Gene Therapy in Prostate Cancer".

Matus Studeny et al.; Cancer Research 62, pp. 3603-3608, Jul. 1, 2002; "Bone Marrow-derived Mesenchymal Stem Cells as Vehicles for Interferon-Delivery into Tumor".

Akira Nakamizo et al.; Cancer Res 2005; 65: (8). Apr. 15, 2005 pp. 3307-3318; "Human Bone Marrow-Derived Mesenchymal Stem Cells in the Treatment of Gliomas".

Niess et al Annals of Surgery vol. 254, No. 5, Nov. 2011; pp. 1-10 "Selective Targeting of Genetically Engineered Mesenchymal Stem Cells to Tumor Stroma Microenvironments Using Tissue-Specific Suicide Gene Expression Suppresses Growth of Hepatocellular Carcinoma".

Altanerova, V. et al. 2012 "Human adipose tissue-derived mesenchymal stem cells expressing yeast cytosinedeaminase::uracil phosphoribosyltransferase inhibit intracerebral rat glioblastoma" *Int. J. Cancer* 130: 2455-2463.

Sun, Z. et al. 2014 "The roles of mesenchymal stem cells in tumor inflammatory microenvironment" *J Hematology & Oncology* 7: 14.

* cited by examiner active region (1,8 kbp) of pcDNA3-eGFP (6,1 kbp)

A

B

| RANTES | HSV-Thymidine kinase | | pCAG | Puromycin resistance |
|---|---|---|---|---|
| Tie-2 | Cytosine deaminase | | EF1alpha | Neomycin resistance |
| | | | PGK | Ouabain resistance |
| | | | CMV | Hygromycine B |
| | | | SFFV | CD34 |

GENETICALLY MODIFIED MESENCHYMAL STEM CELL THAT EXPRESS AN EXOGENOUS CYTOTOXIC PROTEIN

This application is the U.S. national stage application of PCT International Application No. PCT/EP2010/054844, filed Apr. 13, 2010, which claims priority to U.S. Provisional Application No. 61/168,787, filed Apr. 13, 2009, the contents of all such applications being incorporated herein by reference in their entirety.

Throughout this application, various publications are cited. The disclosure of these publications is hereby incorporated by reference into this application to describe more fully the state of the art to which this invention pertains.

BACKGROUND OF THE INVENTION

An emerging paradigm suggests that malignant cells exist in a complex cellular and extracellular microenvironment that significantly influences the initiation and maintenance of the malignant phenotype.[1,2] Solid tumors can be seen to be composed of the malignant cell as well as the supporting cells that comprise the stroma including fibroblasts, endothelium, pericytes, lymphatics and generally, a mononuclear infiltrate.[2-6] These stromal cells are so vital to the survival of the tumor that they have become an important target for chemotherapeutic intervention.

Mesenchymal stem cells (MSCs) are pluripotent progenitor cells that contribute to the maintenance and regeneration of diverse tissues[7,8]. MSCs can be found in many tissues where they serve as local sources of stem cells, such as bone marrow, blood or different sources of mesenchymal tissue. MSCs contribute to tissue remodelling after injury or during chronic inflammation. The damaged tissue is thought to release specific endocrins that then lead to the mobilization of multi-potent MSCs and their subsequent recruitment to the site of injury. MSCs are also strongly attracted to tumor stroma. MSCs infused into the blood in experimental animals localize to malignancies. Once there, MSCs may contribute to diverse cell types that comprise tumor stroma including tumor vasculature and stromal fibroblasts In breast cancer, Karnoub et al. recently showed that MSCs at the tumor site release a small protein, the chemokine CCL5. CCL5 can act as a chemoattractant for diverse stromal cells[9,10] and its expression is associated with increased tumour neovascularization. In addition, CCL5 may contribute to cancer growth and metastasis through the recruitment of a number of stromal cell types to sites of primary tumor growth.[9,11,12]

It has recently been shown that the CD34⁻ subpopulation of MSC progenitors undergo recruitment to the growing tumor and contribute to tumor neoangiogenesis through their differentiation into new vascular endothelial cells (ECs) or pericytes.[13-15] Importantly, these and related direct effects can be observed following the direct injection of MSCs into the peripheral circulation.[16]

There exists an unmet need for stem cell-based therapies that employ cytotoxic protein expression based on proximity with tumor stromal tissue per se for cytotoxic protein expression, rather than cytotoxic protein expression based on proximity with tumor tissue undergoing angiogenesis. This need is particularly acute regarding treatment of metastatic tumors that have not yet undergone angiogenesis.

SUMMARY OF THE INVENTION

One embodiment of this invention provides a method for treating a subject afflicted with a tumor comprising introducing into the subject's bloodstream a therapeutically effective number of genetically modified mesenchymal stem cells, wherein each genetically modified mesenchymal stem cell contains an exogenous nucleic acid comprising (i) a cytotoxic protein-encoding region operably linked to (ii) a promoter or promoter/enhancer combination, whereby the cytotoxic protein is selectively expressed when the genetically modified mesenchymal stem cells come into proximity with the tumor's stromal tissue.

Another embodiment of the invention also provides genetically modified mesenchymal stem cells for use in any of the methods for treating a subject afflicted with a tumor disclosed in this patent application.

This invention also provides a method for treating a human subject afflicted with a pancreatic tumor comprising introducing into the subject's bloodstream from about $1\times10^5$ to about $1\times10^9$ cells/kg body weight of genetically modified CD34⁻ stem cells, wherein (a) each genetically modified CD34⁻ stem cell contains an exogenous nucleic acid comprising (i) a Herpes simplex viral thymidine kinase-encoding region operably linked to (ii) a RANTES promoter, (b) the subject is treated with ganciclovir in a manner permitting the Herpes simplex viral thymidine kinase to render the ganciclovir cytotoxic, and (c) the introduction of the genetically modified mesenchymal stem cells is not preceded, accompanied or followed by myeloablation.

This invention further provides a genetically modified mesenchymal stem cell comprising an exogenous nucleic acid comprising (i) a cytotoxic protein-encoding region operably linked to (ii) a promoter or promoter/enhancer combination, whereby the cytotoxic protein is selectively expressed when the genetically modified mesenchymal stem cell comes into proximity with a tumor's stromal tissue.

Yet a further embodiment of the invention is directed to a retroviral packaging cell comprising:

a retroviral vector including (i) a cytotoxic protein-encoding region operably linked to (ii) a promoter or promoter/enhancer combination, inducible by inflammatory mediators, and a gene encoding a viral surface protein providing a tropism for mesenchymal or CD34⁻ stem cells.

Further the retroviral packaging cell also comprises genes encoding structural proteins and enzymes for the production of pseudotyped virions from the packaging cell.

Finally, this invention provides a genetically modified human CD34⁻ stem cell comprising an exogenous nucleic acid comprising (i) a Herpes simplex viral thymidine kinase-encoding region operably linked to (ii) a RANTES promoter.

Figure 1A:
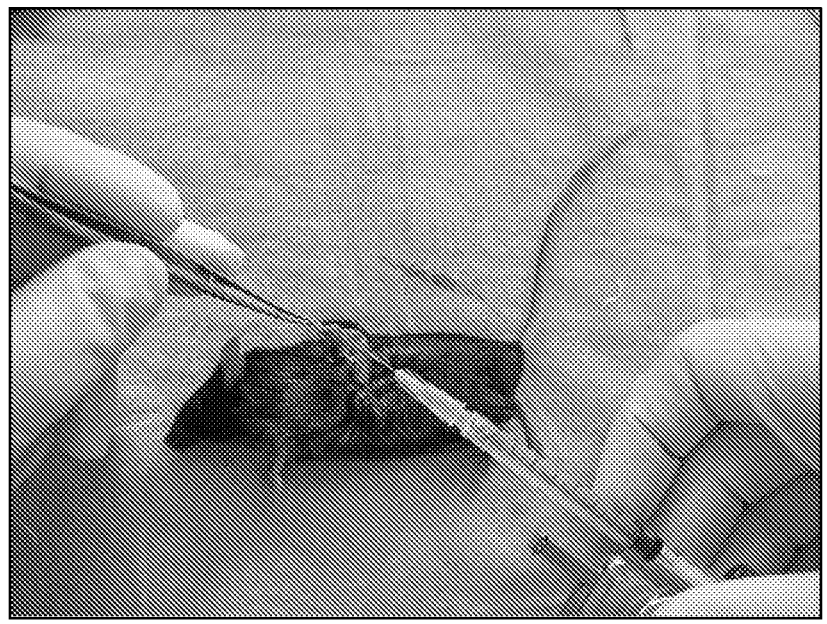
FIG. 1

(A) With a 1 cm incision at the left flank, the pancreas was exposed. A 1 ml syringe was used to inject 150,000 Panc02 pancreatic cancer cells into the pancreas. (B) Two weeks following the procedure, all mice grew palpable tumors and were randomized into the respective experimental groups.

FIG. 2

Modified Boyden Chamber assays were used to evaluate the migratory response of C57B16 MSC to conditioned media derived from Panc02 cells. The results show a dose-dependent induced migration of the MSC to the Panc02-derived growth media.

FIG. 3

The ability of MSCs (engineered to constitutively express eGFP under control of the CMV promoter) to infiltrate implanted Panc02 tumor was examined. Three times a week, 500,000 cells were injected intravenously into mice with growing pancreatic tumors. After five weeks, the mice were sacrificed and the tumors removed and analyzed for the expression of GFP. (A) Results show a strong GFP expression associated with the tumor. (B) The adoptive transfer of MSC was found to increase growth of the implanted tumor over the course of the experiment.

FIG. 4

The CCL5 promoter provides increased selectivity of reporter gene expression to MSC targeting the Panc02 tumor. MSCs were engineered to express either RFP or eGFP under the control of the CCL5 promoter. Following injection of 500,000 cells per week over three weeks, the animals were sacrificed and the tumor examined for reporter gene expression by fluorescence microscopy. Both eGFP (A) and RFP-(B) reporter genes driven by the CCL5 promoter showed expression within the tumor environment. More precise tumor morphology was observed by immunohistochemistry on fixed tissue sections using an RFP specific polyclonal antibody (C and D). (C) Results show a focal expression of RFP in stromal regions of the tumor (100×). (D+E) Similar tumor samples at a higher magnification (200×, 500× respectively) show extensive infiltration of MSC showing expression of the RFP reporter gene in the tumor environment.

FIG. 5

Application of MSC engineered to express HSV-TK under the control of the CCL5 promoter, in conjunction with GVC as a therapeutic modality for pancreatic carcinoma. (A) Overview of the construct used to engineer the MSC to express the HSV-TK suicide gene. (B) For a therapeutic regimen, 500,000 CCL5-TK engineered MSCs were injected intravenously. The cells were given three days to undergo recruitment to the growing tumor and activate expression of the TK gene. The mice received once-daily intravenous injections of 7.5 mg GVC for four days, followed by one day of rest. The mice were then again injected with the engineered stem cells, and the cycle was repeated for the duration of the experiment. After 3 cycles (36 days after tumor induction or 21 days after first MSC injection) the animals were sacrificed and tumor growth was evaluated. (C) Examples of tumors excised from animals treated with vehicle controls, engineered MSC controls (RFP, eGFP) and HSV-TK/GCV-treatment. (D) HSV-TK/GCV treatment resulted in a significant reduction in tumor growth over the course of the experiment.

FIG. 6

Schematic overview of the transgene cassette with several examples of genetic elements. An inducible promoter (pInd) is linked to a cytotoxic protein-encoding region. A second constitutive cellular or viral promoter (pConst) is linked to a selection marker gene. The two units may be separated by an insulator sequence (+/− insulator).

FIG. 7

Figure 6:
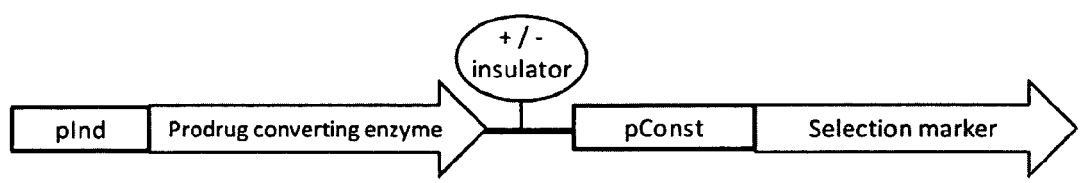

Overview of retroviral vectors carrying the transgene cassette for the genetic modification of MSC depicted in FIG. 6. Vector production will be driven from the promoter activity of the U3-region in the 5' long terminal repeat (LTR). The 5' U3-region may be replaced by other viral promoters. The packaging signal Ψ facilitates the incapsidation of the vector genome into vector particles. For the production lentiviral particles additional elements like rev responsive element (RRE) and the central poly purine tract (cPPT) are necessary. The optional addition of the woodchuck hepatitis post-transcriptional regulatory element (wPRE) will help to increase vector titer and transgene expression. An inducible promoter (pInd) is linked to the cytotoxic protein-encoding region. A second constitutive cellular or viral promoter (pConst) is linked to a selection marker gene. The two units may be separated by an insulator sequence (+/− insulator).

FIG. 8

Plasmid map of lentiviral vector for the expression of HSV tk under the control of the RANTES promoter.

FIG. 9

RANTES mRNA expression after induction of MSCs with TNFα (10 ng/ml) and IFNγ (10 ng/ml). Relative RANTES mRNA amounts were calculated using the ΔΔCT method with the 0h, non-induced sample as normalization value. Mean values from two biological samples are shown.

FIG. 10

Treatment of hMSCs with ganciclovir leads to specific cell death after induction of the RANTES promoter with TNFα and IFNγ. Representative microscopic picture of hMSCs that were not treated (A), induced with TNFα and IFNγ (B), treated only with ganciclovir (C) or first induced with TNFα and IFNγ and then treated with ganciclovir (D). 100× magnification.

DETAILED DESCRIPTION OF THE INVENTION

Terms

In this application, certain terms are used which shall have the meanings set forth as follows.

As used herein, a cell is "allogenic" with respect to a subject if it or any of its precursor cells are from another subject of the same species.

As used herein, a cell is "autologous" with respect to a subject if it or its precursor cells are from that same subject.

As used herein, "CD34⁻ stem cell" shall mean a stem cell lacking CD34 on its surface. CD34⁻ stem cells, and methods for isolating same, are described, for example, in Lange C. et al., Accelerated and safe expansion of human mesenchymal stromal cells in animal serum-free medium for transplantation and regenerative medicine. *J. Cell Physiol.* 2007, Apr. 25 [Epub ahead of print].

As used herein, "cytotoxic protein" shall mean a protein that, when present in, on and/or in proximity with a cell, causes that cell's death directly and/or indirectly. Cytotoxic proteins include, for example, suicide proteins (e.g. HSV-tk) and apoptosis inducers. Cytotoxic genes include null genes, siRNA or miRNA for gene knockdown (e.g. CCR5−/−). A number of suicide gene systems have been identified, including the herpes simplex virus thymidine kinase gene, the cytosine deaminase gene, the varicella-zoster virus thymidine kinase gene, the nitroreductase gene, the *Escherichia coli* gpt gene, and the *E. coli* Deo gene. Cytosine deaminase; Cytochrome P450; Purine nucleoside phosphorylase; Carboxypeptidase G2; Nitroreductase. As detailed in: Yazawa K, Fisher W E, Brunicardi F C: Current progress in suicide gene therapy for cancer. World J. Surg. 2002 July; 26(7): 783-9. Cytotoxic factors include the following: (i) homing factors such as chemokines and mucin chemokine GPI fusions (chemokine derived agents can be used to facilitate the directed recruitment of engineered stem cells, see, e.g., PCT International Application No. PCT/EP2006/011508, regarding mucin fusions anchored with GPI); (ii) viral antigens (measles, chicken pox) as cytotoxic proteins; and (iii) Her2/neu antigens which can be presented on the surfaces of engineered stem cells, followed by administration of her-2/neu antibody, and CamPath® (Alemtuzumab) directed against a CD52 epitope.

As used herein, a nucleic acid is "exogenous" with respect to a cell if it has been artificially introduced into that cell or any of that cell's precursor cells.

As used herein, a stem cell is "genetically modified" if either it or any of its precursor cells have had nucleic acid artificially introduced thereinto. Methods for generating genetically modified stem cells include the use of viral or non-viral gene transfer (e.g., plasmid transfer, phage integrase, transposons, AdV, AAV and Lentivirus).

As used herein, "introducing" stem cells into a subject's bloodstream shall include, without limitation, introducing such cells into one of the subject's veins or arteries via injection. Such administering can also be performed, for example, once, a plurality of times, and/or over one or more extended periods. A single injection is preferred, but repeated injections over time (e.g., daily, every three days, weekly, bi-weekly, monthly, quarterly, half-yearly or yearly) may be necessary in some instances. Such administering is also preferably performed using an admixture of stem cells and a pharmaceutically acceptable carrier. Pharmaceutically acceptable carriers are well known to those skilled in the art and include, but are not limited to, 0.01-0.1 M and preferably 0.05 M phosphate buffer or 0.8% saline. Additionally, such pharmaceutically acceptable carriers can be aqueous or non-aqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions and suspensions, including saline and buffered media. Parenteral vehicles include sodium chloride solution, Ringer's dextrose, dextrose and sodium chloride, lactated Ringer's and fixed oils. Intravenous vehicles include fluid and nutrient replenishers, electrolyte replenishers such as Ringer's dextrose, those based on Ringer's dextrose, and the like. Fluids used commonly for i.v. administration are found, for example, in Remington (34). Preservatives and other additives may also be present, such as, for example, antimicrobials, antioxidants, chelating agents, inert gases, and the like.

"Mesenchymal stem cells" (also referred to as "MSCs") can give rise to connective tissue, bone, cartilage, and cells in the circulatory and lymphatic systems. Mesenchymal stem cells are found in the mesenchyme, the part of the embryonic mesoderm that consists of loosely packed, fusiform or stellate unspecialized cells. As used herein, mesenchymal stem cells include, without limitation, CD34⁻ stem cells.

In one embodiment of the invention, the MSCs are fibroblast like plastic adherent cells defined as multipotent mesenchymal stromal cells in Horwitz et al.[49] and also include CD34– cells. For the avoidance of any doubt, the term "multipotent mesenchymal stromal cells" also includes a subpopulation of mesenchymal stem cells and their precursors, which subpopulation is made up of pluripotent self-renewing cells capable of differentiation into specific, multiple cell types in vivo.

As used herein, "myeloablation" shall mean the severe or complete depletion of bone marrow cells caused by, for example, the administration of high doses of chemotherapy or radiation therapy. Myeloablation is a standard procedure and is described, for example, in Deeg (33).

As used herein, "nucleic acid" shall mean any nucleic acid molecule, including, without limitation, DNA, RNA and hybrids thereof. The nucleic acid bases that form nucleic acid molecules can be the bases A, C, G, T and U, as well as derivatives thereof. Derivatives of these bases are well known in the art, and are exemplified in PCR Systems, Reagents and Consumables (Perkin Elmer Catalogue 1996-1997, Roche Molecular Systems, Inc., Branchburg, N.J., USA).

As used herein, a cytotoxic protein-encoding nucleic acid region is "operably linked" to a promoter or promoter/enhancer combination if such promoter or promoter/enhancer combination causes the expression of the cytotoxic protein under appropriate circumstances.

As used herein, a "polypeptide" means a polymer of amino acid residues. A "peptide" typically refers to a shorter polypeptide (e.g., 10 amino acid residues), and a "protein" typically refers to a longer polypeptide (e.g., 200 amino acid residues). The amino acid residues can be naturally occurring or chemical analogues thereof. Polypeptides can also include modifications such as glycosylation, lipid attachment, sulfation, hydroxylation, and ADP-ribosylation.

As used herein, in "proximity with" a tissue includes, for example, within 1 mm of the tissue, within 0.5 mm of the tissue and within 0.25 mm of the tissue.

The term "RANTES" promoter is used herein synonymously with the term "CCL5" promoter.

As used herein, a cytotoxic protein is "selectively expressed" when a genetically modified mesenchymal stem cell encoding same comes into proximity with tumor stromal tissue, if the cytotoxic protein is expressed in that milieu more than it is expressed in any other milieu in the subject. Preferably, the cytotoxic protein is expressed in that milieu at least 10 times more than it is expressed in any other milieu in the subject.

As used herein, "subject" shall mean any animal, such as a human, non-human primate, mouse, rat, guinea pig or rabbit.

As used herein, "treating" a subject afflicted with a disorder shall mean slowing, stopping or reversing the disorder's progression. In the preferred embodiment, treating a subject afflicted with a disorder means reversing the disorder's progression, ideally to the point of eliminating the disorder itself. As used herein, ameliorating a disorder and treating a disorder are equivalent.

As used herein, "tumor" shall include, without limitation, a prostate tumor, a pancreatic tumor, a squamous cell carcinoma, a breast tumor, a melanoma, a basal cell carcinoma, a hepatocellular carcinoma, testicular cancer, a neuroblastoma, a glioma or a malignant astrocytic tumor such as glioblastma multiforme, a colorectal tumor, an endometrial carcinoma, a lung carcinoma, an ovarian tumor, a cervical tumor, an osteosarcoma, a rhabdo/leiomyosarcoma, a synovial sarcoma, an angiosarcoma, an Ewing sarcoma/PNET and a malignant lymphoma. These include primary tumors as well as metastatic tumors (both vascularized and non-vascularized).

As used herein, a cell is "xenogenic" with respect to a subject if it or any of its precursor cells are from another subject of a different species.

As used herein the term "tumor's stromal tissue" includes the connective, structural tissue around and in proximity to a tumor, which comprises various cells such as fibroblasts/myofibroblasts, glial, epithelial, fat, vascular, smooth muscle, and immune cells. Tumor stroma also provides the extracellular matrix and extracellular molecules[53].

As used herein the term "inflammatory mediators" includes immune modulatory molecules that act at the site of tissue damage and tumor growth, and mediate a pro- and anti-inflammatory response to the tissue damage and tumor growth. Non-limiting examples of inflammatory mediators are cytokines, and eicosanoides. Tumor cells and surrounding stromal cells are known to produce numerous pro-inflammatory mediators like, pro-inflammatory cytokines and proteases that coordinate inflammatory reactions. Examples for such mediators are TNF-alpha and IL-6 Additionally, tumor cells and stromal cells are able to suppress immune responses through secretion of anti-inflammatory molecules, like TGF-beta, IL-10 and M-CSF, which e.g inhibit dendritic cell maturation[54].

Embodiments of the Invention

This invention provides a method for treating a subject afflicted with a tumor comprising introducing into the subject's bloodstream a therapeutically effective number of genetically modified mesenchymal stem cells, wherein each genetically modified mesenchymal stem cell contains an exogenous nucleic acid comprising (i) a cytotoxic protein-encoding region operably linked to (ii) a promoter or promoter/enhancer combination, whereby the cytotoxic protein is selectively expressed when the genetically modified mesenchymal stem cells come into proximity with the tumor's stromal tissue.

The treated subject can be any animal, and is preferably a human. The treated tumor can be primary or metastatic, and can be vascularized or not vascularized. Preferably, the tumor is metastatic and not vascularized. The tumor can be, for example, a prostate tumor, a breast tumor, a pancreatic tumor, a squamous cell carcinoma, a breast tumor, a melanoma, a basal cell carcinoma, a hepatocellular carcinoma, testicular cancer, a neuroblastoma, a glioma or a malignant astrocytic tumor such as glioblastma multiforme, a colorectal tumor, an endometrial carcinoma, a lung carcinoma, an ovarian tumor, a cervical tumor, an osteosarcoma, a rhabdo/leiomyosarcoma, a synovial sarcoma, an angiosarcoma, an Ewing sarcoma/PNET and a malignant lymphoma. Preferably, the tumor is a pancreatic tumor. In another preferred embodiment, the stromal tissue of the treated tumor comprises fibroblast-like cells.

Mesenchymal stem cells can be isolated from various sources: e.g. Bone marrow, umbilical cord blood, (mobilized) peripheral blood and adipose tissue[49]. In a further preferred embodiment, the genetically modified mesenchymal stem cells are CD34− stem cells. Additionally, the genetically modified mesenchymal stem cells can be allogenic, autologous or xenogenic with respect to the subject. In the instant methods employing genetically modified stem cells, the exogenous genes are expressed, i.e., "turned on", when the stem cells (i) come into proximity with the appropriate cells in target tissue, (ii) differentiate, and/or (iii) fuse with the appropriate cells in target tissue.

In this invention, the introduction of the genetically modified mesenchymal stem cells is preferably not preceded, accompanied or followed by myeloablation.

Another embodiment of the invention provides mesenchymal or CD34− stem cells for use in any of the methods for treating a subject afflicted with a tumor. In particular the mesenchymal or CD34− stem cells can include a promoter or promoter/enhancer combination, which is inducible by inflammatory mediators and which controls the transcription of the cytotoxic protein-encoding region. These inflammatory mediators can be released by the tumor's stromal tissue so that the expression of the cytotoxic protein in the mesenchymal stem cells is induced when the stem cells come into proximity with the tumor's stromal tissue. The inflammatory mediators can for example be cytokines, such as TNFα or IFNγ. In particular the promoter can be the RANTES promoter, which can inter alia be induced by TNFα or IFNγ[35]. The RANTES promoter also could be induced by differentiative signals in the context of the differentiation of MSCs. Further examples of promoters, which are inducible by pro-inflammation mediators are the NF-kB-responsive element[36] and in general promoters, which can be induced by IL1β or TNF α[37].

Additionally, promoters activated by anti-inflammatory mediators (e.g. TGF-beta) can be used to achieve a targeted expression the cytotoxic protein in the mesenchymal stem cells. Examples are promoters which contain Smad-binding elements[55].

Using promoters, which are inducible by inflammation mediators, enables a selective treatment of tumors, which have not yet undergone angiogenesis.

The stem cells for use in any of the therapeutic methods of the invention can further comprise a (iii) selection marker gene operably linked to (iv) a constitutive promoter or promoter/enhancer combination. The selection marker gene can comprise an antibiotic resistance gene, such as a gene conferring resistance to Puromycin, Neomycin or Ouabain[38]. The antibiotic resistance genes can be used in order to select for genetically modified mesenchymal stem cells under the presence of the antibiotic and to suppress unmodified mesenchymal stem cells, which should not be used in tumor treatment due to their tumor promoting potential. Additional or as an alternative to an antibiotic resistance gene a gene encoding a surface marker protein can be used, which is only expressed on the surface of genetically modified mesenchymal stem cells. Non-limiting examples for surface marker proteins are splice variants of CD34 and CD24[39-40]. Magnetic beads harboring specific antibodies recognizing the surface marker proteins can be used in order to select for the genetically modified mesenchymal stem cells[41].

The constitutive promoter controlling the transcription of the selection marker gene can be a variety of different promoters such as pCAG[42], EF1α[43], PGK[42], CMV and SFFV[42].

In addition, the stem cells according to various embodiments of the invention can comprise an (v) insulator sequence located between the cytotoxic protein-encoding region and the selection marker gene. The insulator sequence can ensure that the constitutive promoter of the selection marker gene does not influence and "turn on" the transcription of the cytotoxic protein-encoding region in the absence of any inflammatory mediators[44].

Preferably, the cytotoxic protein-encoding region operably linked to the promoter or promoter/enhancer combination and also the selection marker gene operably linked to the constitutive promoter or promoter/enhancer combination are integrated into the stem cell genome. This enables the production of genetically modified mesenchymal stems cells, which are more stable than genetically modified stem cells harboring an extrachromosomal vector.

In a further embodiment of the invention, the genetically modified stem cells further comprise a proviral sequence integrated into the stem cell genome, wherein the cytotoxic protein-encoding region operably linked to the promoter or promoter/enhancer combination and the selection marker gene operably linked to the constitutive promoter or promoter/enhancer combination are part of the proviral sequence. In particular viruses from the family of Retroviridae can be used in order to stable genetically modify mesenchymal stem cells. Examples for retroviruses are lentiviruses, alpha-retroviruses or gamma-retroviruses.

In the following, retroviral vectors including a transgene cassette having two functional units will be described (FIG. 6). The two functional units are:

1. In vitro selection: A constitutive promoter (e.g. CAG-promoter) of cellular or viral origin linked to a selection marker gene like an antibiotic resistance gene (e.g. puromycin-resistance gene) or surface marker gene suitable for magnetic bead-separation (e.g. CD34).

2. By-stander killing: An inducible tumor-specific promoter of cellular or viral origin (e.g. RANTES promoter) linked to cytotoxic protein-encoding region (e.g. coding for Herpes simplex Thymidine kinase)

Optionally, the functional units may be separated by an insulator sequence to prevent promoter interference between the two promoters.

The above described transgene cassette will be integrated into various viral and non-viral vector systems for delivery and stable expression in MSC, such as viral vector systems derived from retroviruses.

The retroviral vectors for the genetic modification of MSC will be derived from alpha-, gamma-retroviruses or (human and non-human) lentiviruses. The retroviral vector systems include the transfer vector backbone, which carries the transgene of interest, i.e. the cytotoxic protein-encoding region and all sequence elements necessary for the reverse transcription and integration of the vector DNA, but is devoid of most or all viral genes, such as gag- pol- and env-genes. The newest generation of retroviral vectors will carry special safety modifications: In these so called self-inactivating (SIN) vectors the 3' U3-region is partially or completely removed to shut down viral promoter activity and to prevent transactivation of neighboring genes in the host cell genome[50].

For the production of vector particles a variable number of helper plasmids is needed which provide the structural proteins, enzyme and envelope proteins in trans[50]. Viral particles can be produced carrying foreign envelope glycoproteins. This process is called pseudotyping. It allows altering the tropism of the vector particles and in some cases enhances vector titer.

The above described transgene cassette will be inserted into a SIN-retroviral vector backbone using standard molecular biology methods and produce viral particles according to standard methods[50].

Figure 7:
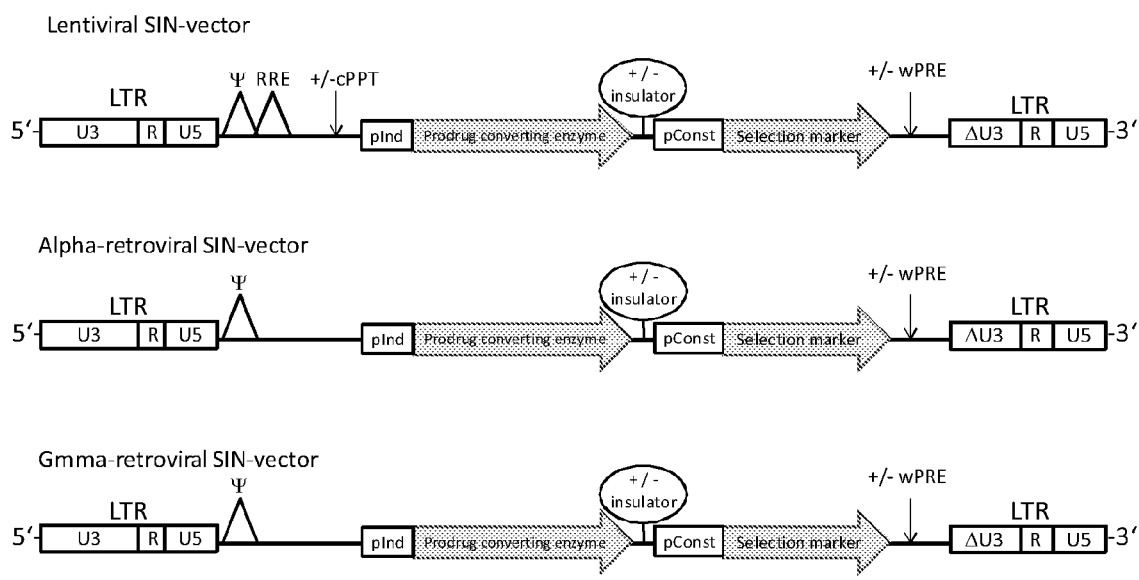

FIG. 7 gives an exemplary overview of alpha- and gamma-retroviral and lentiviral vector constructs, which will carry the mentioned transgene depicted in FIG. 6.

It is planned to pseudotype the vector particles with the glycoprotein of the Lymphocytic choriomeningitis virus (LCMV GP), vesicular stomatitis virus (VSV-g), RD114-TR or gibbon ape leukemia virus (GALV env).

Another alternative method for the genetic modification of mesenchymal stem cells is by chemical (e.g. Lipofectamin) or physical (e.g. electroporation) transfection. Afterwards transfected cells can be selected as described above to select stably transfected MSC, where the transgene cassette has integrated by chance into the mesenchymal stem cell genome.

Yet another alternative for the genetic modification of MSCs is by using non-viral vector systems derived from transposons. After flanking of the above described expression cassette with terminal inverted repeats, the construct can be transferred into MSC via transfection. If a Transposase like Sleeping Beauty[51] or Piggybac[52] is expressed in trans during the transfection, the expression cassette will be stably integrated into the genome of the MSC.

The genetically modified mesenchymal stem cells according to some embodiments of the invention can be prepared by transduction of native mesenchymal stem cells with pseudotyped virions, expressing foreign glycoproteins on their surface, which alter the tropism and often the titer of the virion.

The pseudotyped virions can be generated by the help of retroviral packaging cells comprising:
- a retroviral vector including (i) a cytotoxic protein-encoding region operably linked to (ii) a promoter or promoter/enhancer combination, inducible by inflammatory mediators, and
- a gene encoding a viral surface protein providing a tropism for mesenchymal or CD34− stem cells.

Further the retroviral packaging cell also comprises genes encoding structural proteins and enzymes for the production of pseudotyped virions from the packaging cell, such as the gag-, pol- and env-genes, which enable the assembly of the pseudotyped virions.

Preferably these genes encoding structural proteins and enzymes are located on a different vector than the gene encoding a viral surface protein providing a tropism for mesenchymal or CD34− stem cells in order to produce virions, which are infectious but not capable of replication. These pseudotyped virions harbor the cytotoxic protein-encoding region operably linked to (ii) a promoter or promoter/enhancer combination and express the viral surface protein. Normally the supernatant of the retroviral packaging cells containing the pseudotyped virions will be used for the transduction of the mesenchymal stem cells.

The gene encoding a viral surface protein providing a tropism for mesenchymal or CD34− stem cells (pseudotyping) can be a large variety of glycoproteins conferring a broad host tropism such as the Lymphocytic choriomeningitis virus (LCMV GP)[45], vesicular stomatitis virus (VSV-g)[45], RD114-TR[46] or gibbon ape leukemia virus (GALV env)[47].

As already mentioned above, the promoter or promoter/enhancer combination can be inducible by cytokines or other inflammatory mediators. In a preferred embodiment the promoter is the RANTES promoter. The retroviral packaging cell can also include further genes and promoters In another particular embodiment of the invention, the cytotoxic protein ideally is Herpes simplex viral thymidine kinase, and the subject ideally is treated with ganciclovir in a manner permitting the Herpes simplex viral thymidine kinase to render the ganciclovir cytotoxic. Ganciclovir and its methods of use are well known in the art. Another possibility is the use of cytosine deaminase as a cytotoxic protein, which converts 5-fluorocytosine to the toxic compound 5-fluorouracil[48].

In this invention, the therapeutically effective number of genetically modified mesenchymal stem cells includes, without limitation, the following amounts and ranges of amounts: (i) from about $1\times10^5$ to about $1\times10^9$ cells/kg body weight; (ii) from about $1\times10^6$ to about $1\times10^8$ cells/kg body weight; (iii) from about $5\times10^6$ to about $2\times10^7$ cells/kg body weight; (iv) from about $5\times10^6$ to about $1\times10^7$ cells/kg body weight; (v) from about $1\times10^7$ to about $2\times10^7$ cells/kg body weight; (vi) from about $7\times10^6$ to about $9\times10^6$ cells/kg body weight; (vii) about $1\times10^5$ cells/kg body weight; (viii) about $1\times10^6$ cells/kg body weight; (ix) about $5\times10^6$ cells/kg body weight; (x) about $1\times10^7$ cells/kg body weight; (xi) about $6\times10^6$ cells/kg body weight; (xii) about $7\times10^6$ cells/kg body weight; (xiii) about $8\times10^6$ cells/kg body weight; and (ix) about $9\times10^6$ cells/kg body weight. Human body weights envisioned include, without limitation, about 50 kg, about 60 kg; about 70 kg; about 80 kg, about 90 kg; and about 100 kg. These numbers are based on pre-clinical animal experiments and standard protocols from the transplantation of MSCs.

This invention also provides a method for treating a human subject afflicted with a pancreatic tumor comprising introducing into the subject's bloodstream from about 5×10⁶ to about 2×10⁷ cells/kg body weight of genetically modified CD34⁻ stem cells, wherein (a) each genetically modified CD34⁻ stem cell contains an exogenous nucleic acid comprising (i) a Herpes simplex viral thymidine kinase-encoding region operably linked to (ii) a RANTES promoter, (b) the subject is treated with ganciclovir in a manner permitting the Herpes simplex viral thymidine kinase to render the ganciclovir cytotoxic, and (c) the introduction of the genetically modified mesenchymal stem cells is not preceded, accompanied or followed by myeloablation. In this method, the tumor is preferably metastatic, and can be vascularized or not. Additionally, the genetically modified mesenchymal stem cells can be allogenic, autologous or xenogenic with respect to the subject.

This invention further provides a genetically modified mesenchymal stem cell comprising an exogenous nucleic acid comprising (i) a cytotoxic protein-encoding region operably linked to (ii) a promoter or promoter/enhancer combination, whereby the cytotoxic protein is selectively expressed when the genetically modified mesenchymal stem cell comes into proximity with a tumor's stromal tissue. Preferably, the mesenchymal stem cell is a human CD34⁻ stem cell. Also preferred is an exogenous nucleic acid comprising a RANTES promoter, wherein the cytotoxic protein is Herpes simplex viral thymidine kinase.

Finally, this invention provides a genetically modified human CD34⁻ stem cell comprising an exogenous nucleic acid comprising (i) a Herpes simplex viral thymidine kinase-encoding region operably linked to (ii) a RANTES promoter.

The various proteins and regulatory sequences used in this invention can be readily obtained by one skilled in the art. For example, the RANTES promoter is disclosed in (22) and can be obtained by the use of ordinary skill. The HSV TK—V00467 Herpes gene can be used for thymidine kinase (ATP:thymidine 5' phosphotransferase, e.c. 2.7.1.21) (type 1 strain CL101).

This invention will be better understood by reference to the Experimental Details which follow, but those skilled in the art will readily appreciate that the specific experiments detailed are only illustrative of the invention as described more fully in the claims which follow thereafter.

Experimental Details

Synopsis

Objective:

To analyze the efficacy of engineered mesenchymal stem cell-based therapy directed towards pancreatic tumor stroma.

Summary Background Data:

Mesenchymal stem cells (MSC) are actively recruited to tumor stroma where they enhance tumor growth and metastases. Upregulation of chemotactic cytokine CCL5 by MSCs within the tumor stroma has been shown to play a central role in this process. Murine MSCs were engineered to express reporter genes or therapeutic genes under control of the CCL5 promoter and adoptively transferred into mice with growing pancreatic tumors. The effect on tumor growth and metastases was then evaluated.

Methods:

MSCs isolated from bone marrow of C57/B16 p53(−/−) mice were stably transfected with Red Fluorescent Protein (RFP), enhanced Green Fluorescent Protein (eGFP) or Herpes simplex virus (HSV) thymidine kinase (tk) gene driven by the RANTES promoter. MSCs were intravenously applied once per week over 3 weeks to mice carrying an orthotopic, syngeneic pancreatic Panc02 tumor.

Results:

eGFP and RFP signals driven by the CCL5 promoter were detected by florescence in treated pancreatic tumor samples. The HSV-tk therapy group treated i.p. with the prodrug ganciclovir (GCV) 5-7 days after stem cell application lead to a 50% reduction of primary pancreatic tumor growth ($p<0,0003$, student's t-test) and reduced liver metastases (30% vs. 100%).

Conclusions:

The active homing of MSCs into primary pancreatic tumor stroma and activation of the RANTES promoter was verified using eGFP- and RFP-reporter genes. In the presence of ganciclovir, HSV-tk-transfected MSCs led to a significant reduction of primary pancreatic tumor growth and incidence of metastases.

Materials and Methods

Mesenchymal Stem Cells

Mesenchymal stem cells were isolated from the bone marrow of C57BL/6 mice homozygous for the targeted deletion of p53 as described.[15] The cells grew adherently and continuously in cell culture. After subcloning, single cell clones were selected and characterized.[15] The cells were transfected with red fluorescent protein (RFP), green fluorescent protein (eGFP) or HSV thymidine kinase linked to the CCL5 promoter. The sequence of the promoter used −972 of the upstream region and the complete 5' untranslated region.[18] In addition, all vectors contained a CMV-controlled Bsr2 Blasticidin resistance gene. Blasticidin was used to select for transfected cells at a concentration of 5 μg/ml. Prior to injection into the mice, the cells were detached from the culture flasks, washed twice with PBS, and re-suspended in PBS.

Modified Boyden Chamber Assay

Directed MSC migration in vitro was performed using a modified Boyden chamber assay.[15] Stem cells migrated against descending concentrations of supernatant of Panc02 syngenic pancreatic carcinoma cells.

Orthotopic Pancreatic Carcinoma Model

C57BL6 mice were obtained from Jackson Labs. All animal experiments were conducted with appropriate permission from the animal rights commission of the state of Bavaria. Two-month-old to three-month-old C57BL/6 mice with an average weight of approximately 20 g were used for implantation of the Panc02 (syngenic to C57BL/6 mice) pancreatic tumor.[19] The mice were anesthetized using Ketamine (100 mg per kg body weight), Xylazine (5 mg per kg body weight) and Atropine. The operation site on the left flank of the mice was shaved and prepared in a sterile manner. With a 1 cm incision at the left flank, the pancreas was exposed. A calibrated push-button device (Hamilton Syringe Company, USA) and a 1 ml syringe with a 30 G needle (both BD Biosciences, Spain) was used to inject 150,000 Panc02 pancreatic cancer cells in a 40 μl PBS solution into the pancreas. Caution was taken to ensure that no pancreatic cancer cells were disseminated into the peritoneum. To this end, a Q-tip was pressed lightly on the injection site for one minute after the needle was pulled out of the pancreas. Following the injection of the tumor cells the peritoneum and skin were closed with interrupted sutures of 4-0 prolene (Braun A G, Germany). Two weeks following the procedure, all mice grew palpable tumors and were randomized into the respective experimental groups. Group A received no stem cells or Ganciclovir injections, group B received unmodified stem cells, group C received C57BL/6 p53−/− CCL5/HSV-tk+ mesenchymal stem cells and GCV injections, group D received C57BL/6 p53−/− CCL5/RFP+ mesenchymal stem cells and group E received C57BL/6 p53−/− CCL5/eGFP mesenchymal stem cells. All stem cell injections were dosed at $0.5 \times 10^6$ cells per week and administered via the tail vein. GCV (Cymeven®, Roche, Germany) injections of group C were at a dose of 1.5 mg and were applied i.p. on days 5 to 7 following the stem cell injections. All mice were sacrificed after three cycles of treatment and the tumors were isolated and weighed. Testing for statistic significance was achieved with an unpaired two-tailed t-test for independent samples.

Fluorescence Microscopy

Tissue samples of the pancreatic tumors were embedded in Tissue-Tek O.C.T. (Miles Inc. USA) and snap-frozen in liquid nitrogen. Cryosections of 5 μm thickness were obtained. DAPI nuclear staining solution (Vectashield "Hard set mounting medium with Dapi", USA) was added to the sections and they were immediately assessed for GFP or RFP fluorescence signals. Photos were obtained using the AxioCam MR microscope camera and pictures of different fluorescence channels were overlaid using the software Photoshop® (Adobe, USA).

MSC Injection and Ganciclovir Treatment

Before injection, the cells were counted and diluted to a final concentration of $1 \times 10^6$ cells/ml PBS. Ganciclovir (GCV) (Cymeven; Roche) was dissolved in $H_2O$ (aqua ad iniectabilia) to a concentration of 10 mg/ml. Cell suspensions were administered with a 26 G needle via the tail vein, drugs via intraperitoneal injections. The treatment started on day 1, with injection of 0.5 ml cells (500,000 cells). On days 5 through 7, Ganciclovir was applied in a daily dose of 60 μg/g BW, e.g. 150 μl for a mouse with 25 g BW. After day 7, treatment cycles were repeated until dissection. During the treatment tumor progression and behaviour were recorded.

Tissue and Tumor Preparation

After dissection, all of the tumors were prepared separately. One third of each tumor was formaldehyde-fixed and embedded in paraffin wax while an additional third was flash-frozen. The last third was conserved in RNAlater solution (Ambion) accordingly to the manufacturer's instructions for later RNA isolation and intended qRT-PCR analysis.

Immunohistochemistry

Immunohistochemistry was performed on 5 μm sections, as previously described.[20] As the primary antibodies, the polyclonal rabbit anti-RFP antibody (Mbl Medical and Biological Laboratories, Japan) was diluted 1:50 in blocking solution (milk+superblock). As the secondary antibody, a polyclonal biotinylated goat anti-rabbit (Linaris, Wertheim-Bettingen, Germany) antibody was diluted 1:300 in milk.

Results

Recruitment of MSCs to Pancreatic Tumors

Figure 1B:
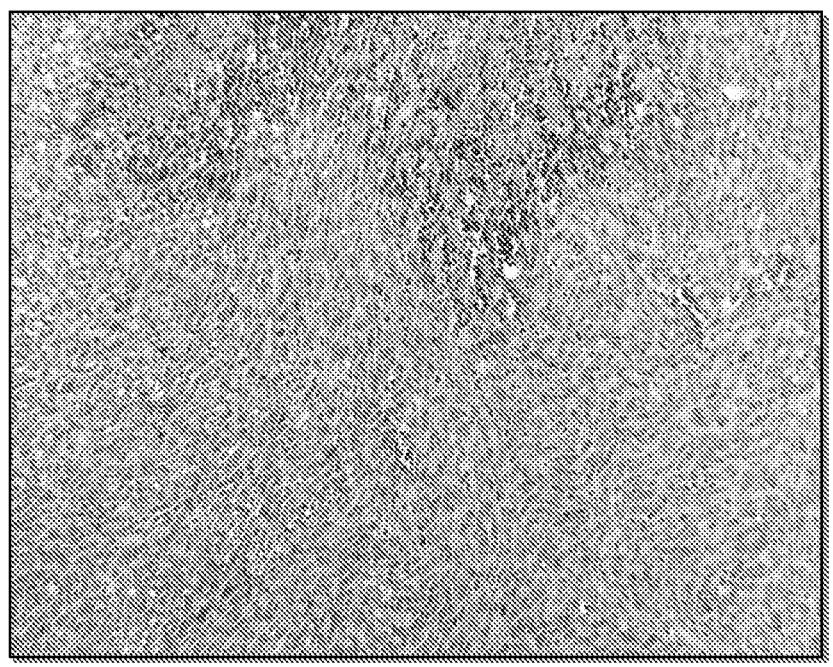

A syngeneic, orthotopic murine pancreatic tumor was previously established in a C57Bl/6 mouse background.[31,32] Tumor cells implanted under the capsule of the pancreas grew and showed a profound tumor vasculature (FIG. 1). CD34− MSCs isolated from bone marrow of P53(−/−) were used to evaluate the efficacy of engineered MSCs for targeting tumor stroma.[15,16,21]

Figure 2:
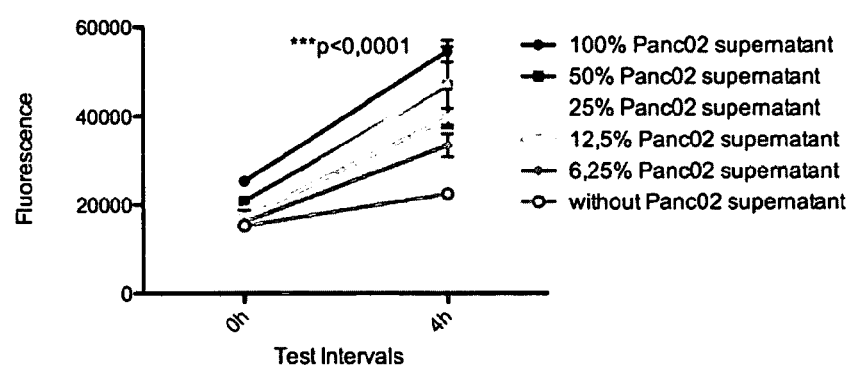

To first evaluate the general tropism of the MSC for the Panc02 tumor, modified Boyden chamber assays were use to study the induced migration of the C57B16 MSC towards tumor-derived factors. The results show a dose-dependant migration of the MSC in response to increasing levels of conditioned tumor growth media (FIG. 2).

Figure 3:
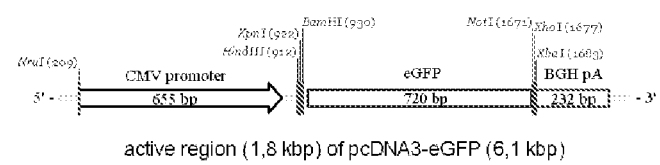
Figure 3:
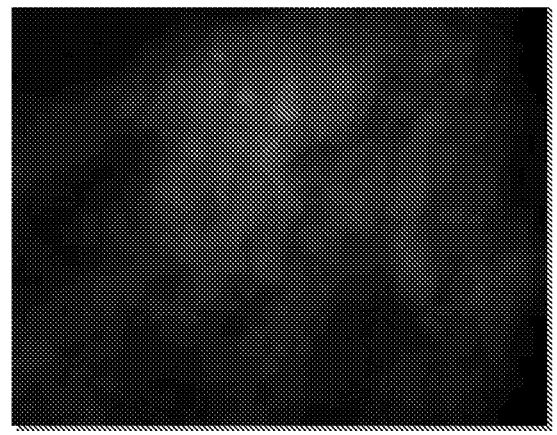
Figure 3:
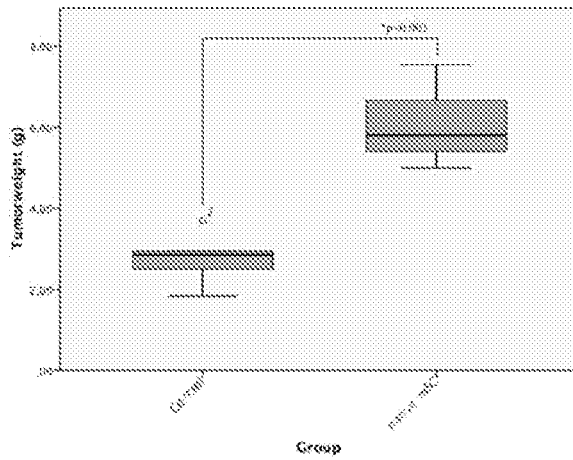

The cells were then engineered with a plasmid containing green fluorescent protein (GFP) under control of the CMV promoter. Once a week, 500,000 cells were injected intravenously into mice with growing pancreatic tumors. After five weeks, the mice were sacrificed and the tumors removed and analyzed for expression of GFP. Results show a strong GFP expression associated with the tumor (FIG. 3A). The cells were also found to migrate to secondary spleen, lymph nodes, thymus, skin and gut (data not shown and (15)). This demonstrates a homing of the systemically injected stem cells to the growing tumor. The i.v. injection of MSC into C57B16 mice with growing pancreatic tumors also resulted in a significant increase in tumor growth (FIG. 3B).

The effect of i.v.-applied MSC metastases to liver, spleen, and peritoneum was also evaluated. Application of MSCs was found to significantly increase metastases to the peritoneum (Table 1).

The CCL5 Promoter Drives Reporter Gene Expression in Tumor Stroma

We then explored the possibility of driving a more controlled expression of reporter genes in the context of MSC recruitment to tumor stroma using the CCL5 promoter. To this end, the P53(−/−) MSC C57/B16 cell line was engineered with a RFP and eGFP reporter genes under the control of the CCL5 promoter.[18,22] The CCL5 promoter is active in diverse tissue types generally in the context of tissue stress or damage.[23-27] The immediate −972 upstream nucleotides and the complete 5' untranslated region to the start of translation were cloned upstream of eGFP or RFP in a vector.

The resultant CCL5-eGFP or RFP stably engineered MSCs showed weak but detectable levels of expression of the reporter via FACS (data not shown). The cells (500,000) were then injected into the peripheral circulation of mice with growing pancreatic tumors every eight days for 21 days.

Figure 4:
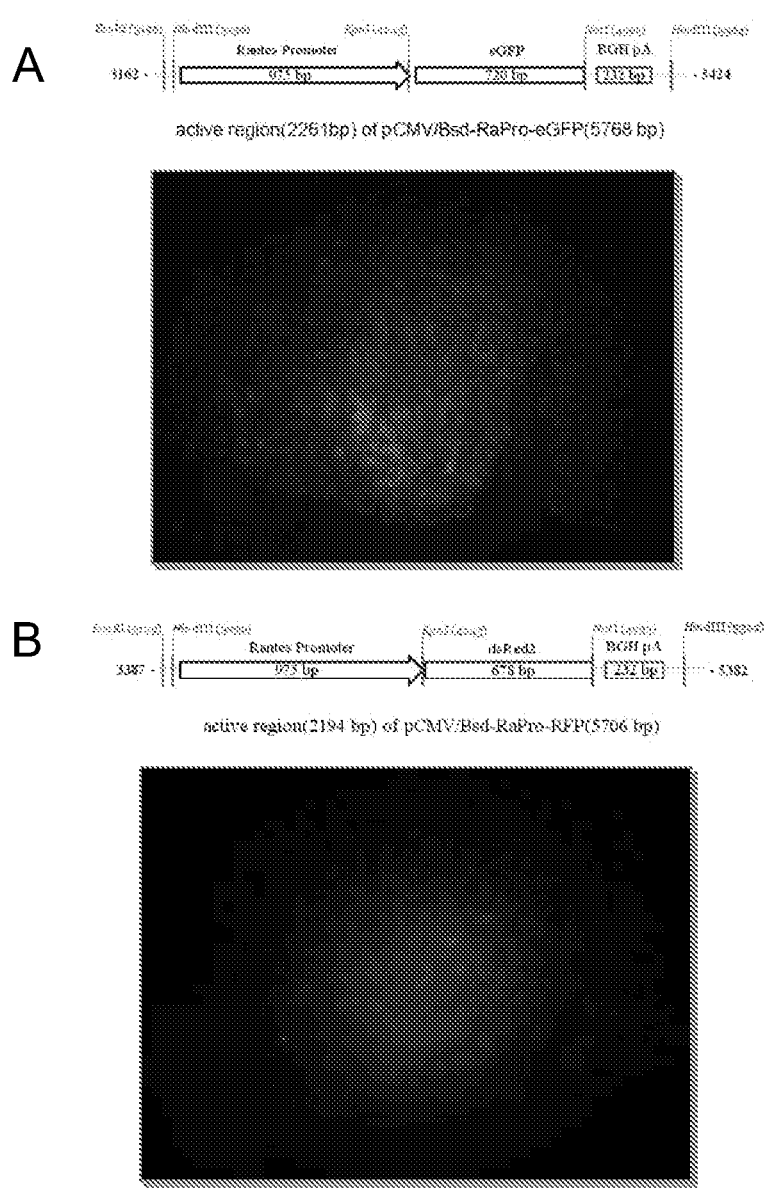
Figure 4:
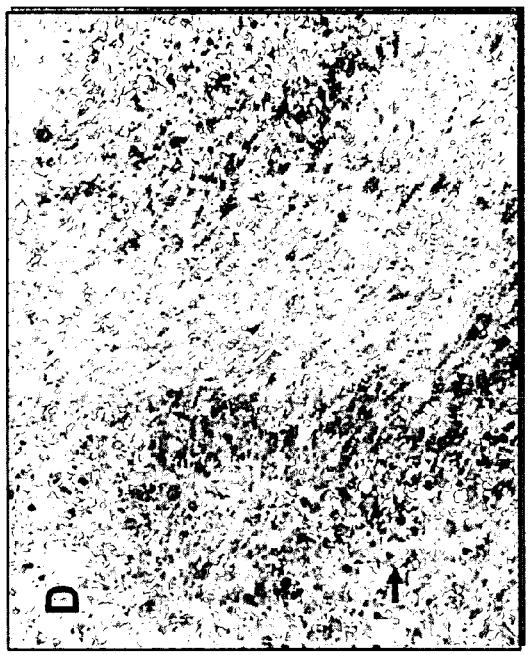
Figure 4:
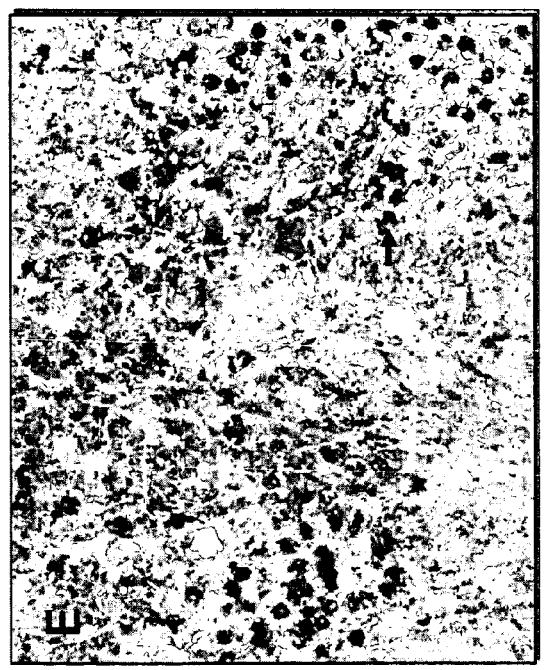
Figure 4:

Three weeks later the mice were sacrificed and the tumor and surrounding tissue was analyzed for RFP and eGFP reporter gene expression by fluorescence microscopy and immunohistochemistry. The results showed expression of RFP and GFP fluorescence in the growing tumor (FIGS. 4A and B). To examine the expression RFP in tissue samples with better morphology, formaldehyde fixed samples were tested for RFP protein expression by immunohistochemistry. RFP expressing MSC were detected throughout the tumor stroma (FIGS. 4C, D and E).

The Use of HSV-tk as a Therapeutic Modality in the Engineered MSCs

In the next phase of the experiment, delivery of therapeutic genes using the CCL5 promoter was examined. To this end, the gene for Herpes simplex thymidine kinase (HSV-Tk)[28] was cloned behind the CCL5 promoter (FIG. 5A).

After $0.5 \times 10^6$ CCL5-tk engineered MSCs were injected, the cells were given three days to undergo recruitment to the growing tumor stroma, undergo differentiation and subsequent expression of the tk gene. The mice then received a course of treatment consisting of once-daily intraperitoneal injections of 1.5 mg GVC for three days. The mice were again injected with the engineered stem cells, and the cycle was repeated for the duration of the experiment (FIG. 5B).

Figure 5:
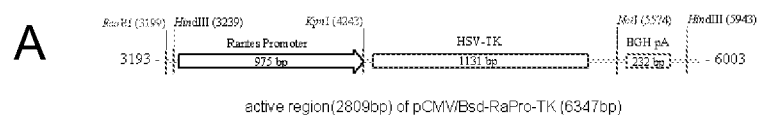
Figure 5:
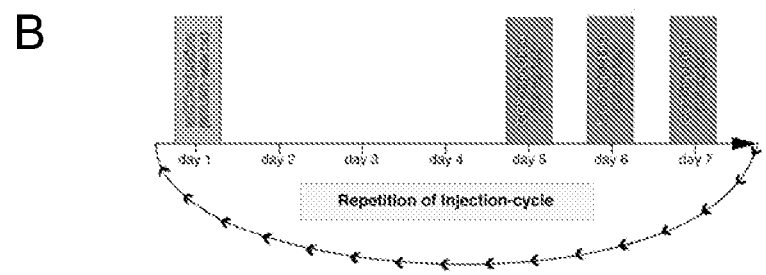
Figure 5:
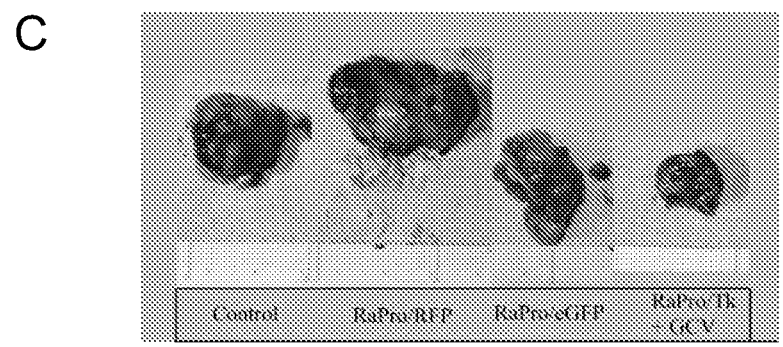
Figure 5:
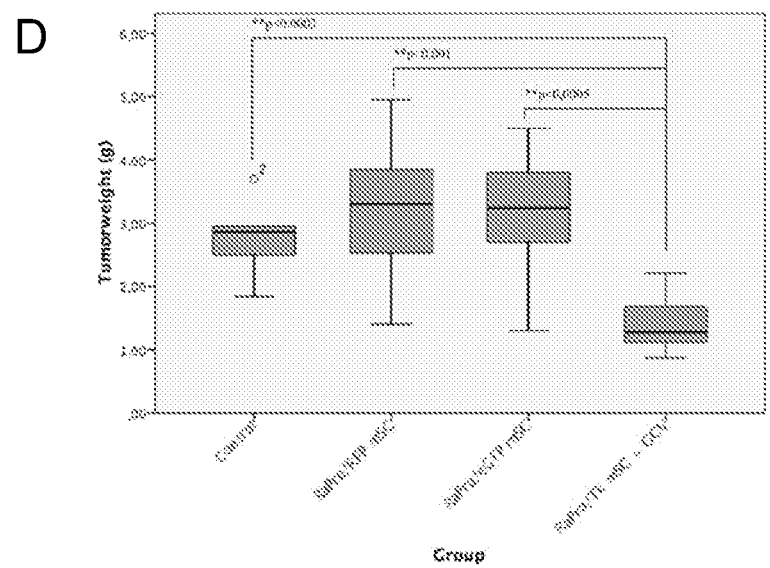

After 36 days, the animals were sacrificed and tumor growth was evaluated (FIGS. 5C and D). Results showed a significant decrease in tumor volume in the group of mice that received the therapeutic CCL5/HSV-Tk stem cell construct with GCV in comparison to control animals with tumors that received no treatment or control MSC(CCL5-RFP MSC and CCL5-eGFP MSC). FIG. 5C shows representative tumors excised upon completion of the experiment. The weights of the tumors show a statistically significant decrease in tumor weight as compared to untreated or treated control animals.

As an additional parameter, liver, spleen, and peritoneum were analyzed for metastases in the context of treatment. While the administration of MSC increased the number of metastases in the peritoneum, treatment with GCV resulted in a significant reduction of metastases in spleen and liver (two-tailed Fisher's exact test) (Table 2). Metastases were evaluated by inspection of spleen, liver, and peritoneum in the situs and palpation of the respective organs.

Discussion

Mesenchymal stem cells are actively recruited to tumor stroma where they contribute to diverse aspects of tumor growth. MSC can function as progenitor cells for tumor vessels and also appear to contribute to the generation of stromal-fibroblast-like cells. The specific influence of tumor-associated stromal cells on tumor growth and on the potential to metastasize is an issue of current research. In preclinical studies of a mamma-carcinoma model, it was shown that mesenchymal stem cells (MSC) within the tumor stroma produce increased levels of the cytokine CCL5. The secretion of CCL5 leads to a higher incidence of lung metastases.

CCL5 secretion is also differentially regulated in pancreatic periacinar myofibroblasts, suggesting a role for these cells in mediating the infiltration and accumulation of inflammatory cells in the pancreas.[29] Among patients with pancreatic cancer, pancreatitis has been significantly associated with polymorphism in the CCL5 promoter.[30] The work herein evaluates the use of engineered MSCs as a therapeutic vehicle for the selective delivery of a suicide gene in the context of tumor stroma on primary tumor growth as well as metastases.

MSCs were engineered to express the herpes simplex virus (HSV) thymidine kinase (TK) under the control of the CCL5 promoter for tissue specific expression. MSCs were transfected using herpes-simplex-virus-thymidine kinase (tk) and under the control of the CCL5 promoter for a more tissue specific gene expression. Tk phosphorylates ganciclovir (GCV), generating a toxin that kills the transfected cells and nearby tumor cells via a bystander effect. HSV-TK gene therapy with ganciclovir forms the basis of a widely-used strategy for suicide gene therapy.[17]

As solid tumors exert a strong homing drive on circulating progenitors, the tumor environment is efficiently targeted using this approach. This targeting of the vehicle stem cells in addition to the tissue-specific gene expression driven by the CCL5 promoter of the suicide gene leads to both high efficacy and a low side effect profile. Furthermore, bone marrow-derived MSC could be obtained from the cancer patients themselves. This would allow for the specific delivery of suicide genes through easy intravenous administration without the need for myeloablation and a bone marrow transplant.

Pancreatic cancer treatment strategies based on preclinical research have not succeeded in significantly extending patient survival. At the time of diagnosis, only 20% of the patients suffering from pancreatic cancer present with localized disease amenable to surgery. Forty percent of the patients present with locally advanced (and therefore, unresectable) disease, and another 40% already suffer from distant metastases. The pancreatic tumor model demonstrated that MSCs play important role in pancreatic carcinoma. The cells actively seek the tumor, as illustrated via migration assays as well as systemic injections of CCL5/RFP MSC. The systemically injected stem cells were found exclusively within the tumor. The ensuing reduction in tumor size and reduced peritoneal carcinosis are promising for the clinical application of a patient-tailored combined stem cell/suicide gene therapy.

Engineered stem cells that are recruited to other tissue niches do not undergo the same program of differentiation, and therefore do not express the therapeutic gene. This approach allows a significant degree of control of the selective expression of the therapeutic gene within a defined microenvironment.

Linking stem cell therapy with selective gene therapy enhances the therapeutic options for the regeneration or replacement of diseased or missing cells, as well as for tumor destruction. Here, it is shown that genetically modified stem cells can serve as a vehicle for the transport of tissue-specific gene therapy to tumors and that MSC engineered with the CCL5-promoter can drive tk expression.

TABLE 1

| | | Group | | |
|---|---|---|---|---|
| | | Control (n = 5) | native mSC (n = 3) | |
| | | Metastases | Metastases | p-value |
| Organ | Spleen | 5 (100%) | 3 (100%) | 1.00 |
| | Liver | 3 (60%) | 3 (100%) | 0.46 |
| | Peritoneum | 0 (0%) | 3 (100%) | 0.018* |

The effect of MSC treatment on the development of metastases. Comparison of vehicle control and animals treated with native MSC (MSC given over a period of three weeks with 500,000 cells weekly). Examination was done by inspection and palpation after 36 days of tumor growth. Numbers express animals with metastases. Significance was tested by two-tailed Fisher's exact test.

TABLE 2

| | | Group | | | | | | |
|---|---|---|---|---|---|---|---|---|
| | | Control (n = 5) | RaPro/RFP (n = 9) | | RaPro/eGFP (n = 6) | | RaPro/Tk + GCV (n = 10) | |
| | | Metastates | Metastates | p-value | Metastates | p-value | Metastates | p-value |
| Organ | Spleen | 5 (100%) | 8 (89%) | 1.00 | 5 (100%) | 1.00 | 3 (30%) | 0.026* |
| | Liver | 3 (60%) | 4 (44.4%) | 1.00 | 2 (33%) | 0.57 | 0 (0%) | 0.022* |
| | Peritoneum | 0 (0%) | 7 (78%) | 0.021* | 4 (67%) | 0.06 | 0 (0%) | 1.00 |

Table 2. The distribution of tumor metastases. Vehicle Control animals and GFP and RFP reporter gene transfected control MSCs were compared to animals treated with the suicide gene therapy. Examination by inspection and palpation after 36 days of tumor growth. Numbers express animals with metastases. Significance was tested by two-tailed Fisher's exact test. All MSC were given over a period of three weeks with 500,000 cells weekly.

Figure 8:
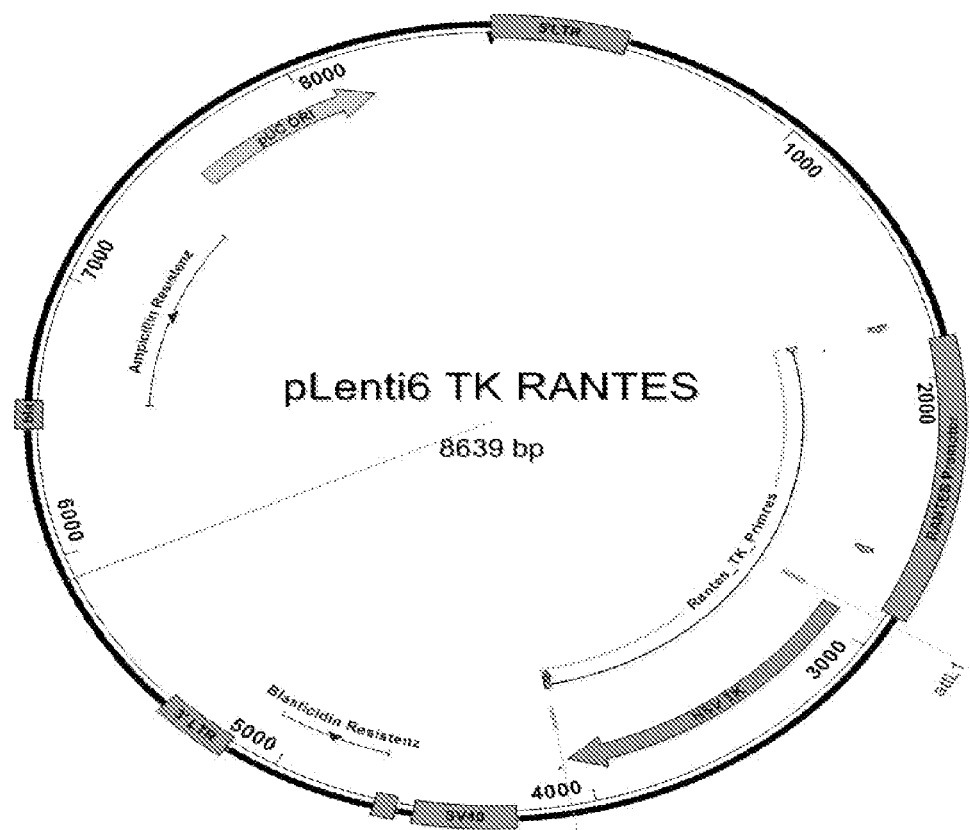

In Vitro Experiments for Stable Transduction of Human MSCs and In Vitro Assay for Induction of HSV Tk Expression Generation of Genetically Modified Human MSCs Human MSCs were incubated over night with replication deficient lentiviruses carrying the vector pLenti6 TK RANTES harboring the HSV tk gene under the control of the RANTES promoter and the blasticidin resistance gene under the control of the SV40 promoter (multiplicity of infection (MOI): 10) (see FIG. 8).

After overnight incubation the virus containing media was removed and replaced with fresh media. The next day blasticidin (6 µg/ml) was added to the cells to select for genetically modified MSCs. Culture media, including blasticidin was changed every 3 to 4 days for a minimum of 6 days.

In Vitro Induction of the RANTES Promoter

It was demonstrated that a combination of the cytokines TNFα (10 ng/ml) and IFNγ (10 ng/ml) leads to an induction of the RANTES promoter in human umbilical vascular endothelial cells (HUVECS)[35].

In our experiments we wanted to demonstrate that the same combination of cytokines also leads to an induction of the endogenous RANTES promoter in MSCs. We wanted to use this assay to be able to induce the expression of the exogenous HSV tk in vitro. Genetically modified MSCs were cultivated for up to 48 h with TNFα and IFNγ or without the cytokines and isolated whole RNA after 0, 24 and 48 h. The RNA (600 ng) was reverse transcribed to cDNA which, in turn, was used in qRT-PCR reactions to quantify endogenous RANTES expression with the LighCycler system (Roche, Primer: for: CCT CAT TGC TAC TGC CCT CT; rev: GGT GTG GTG TCC GAG GAA TA; Universal Probe 16). To assure that same amounts of RNA were used from different samples a housekeeping gene (actin) was used as reference gene (*Universal ProbeLibrary Human ACM Gene Assay*, Roche) and relative amounts were calculated using the ΔΔCT method.

Figure 9:
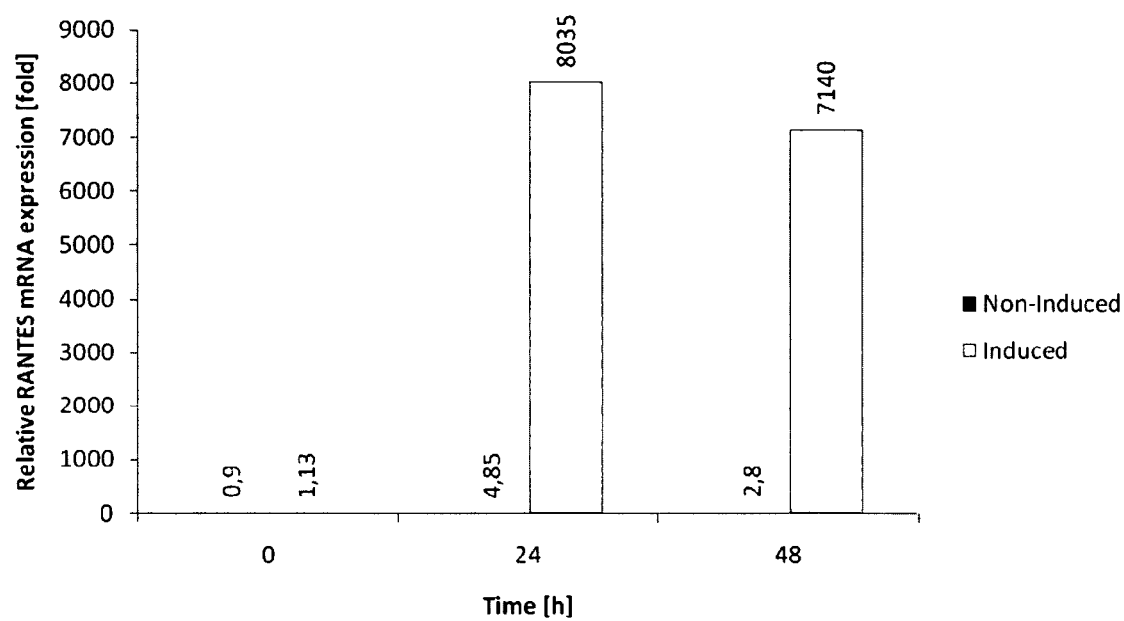

As shown in FIG. 9, we were able to detect a pronounced increase of endogenous RANTES mRNA 24 and 48 h after induction of MSCs with TNFα (10 ng/ml) and IFNγ (10 ng/ml). These findings demonstrate that RANTES expression is induced by TNFα and IFNγ not only in HUVECs but also in human MSCs.

Specific Cell Death of Induced Genetically Modified MSCs After Ganciclovir Treatment After we could demonstrate the inducibility of the endogenous RANTES promoter we went on to investigate if it was possible to induce the expression of the HSV tk which was under the control of the exogenous RANTES promoter and as a consequence promote cell death after treatment of the induced cells with ganciclovir. Genetically modified cells (50000 cells in per 6 well) that were generated as described above were treated for 9 days with TNFα (10 ng/ml) and IFNγ (10 ng/ml) with addition of fresh cytokines every 3 days. Subsequently the cells were incubated for 3 days with 100 µM ganciclovir.

Figure 10:
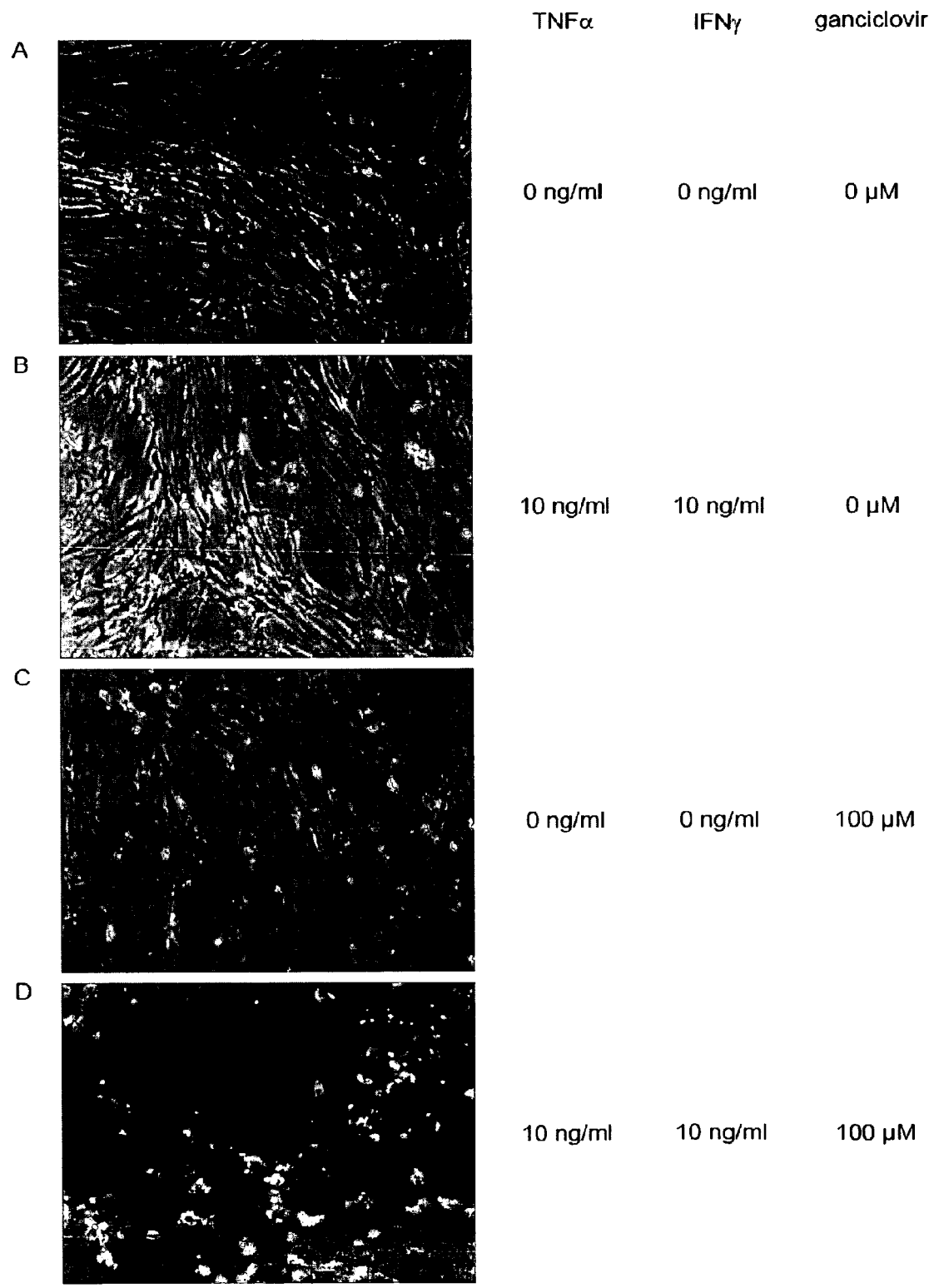

The results clearly demonstrated that genetically modified MSCs which were induced with TNFα and IFNγ and subsequently treated with ganciclovir were not surviving (FIG. 10 D). In contrast to cells that were only induced with TNFα and IFNγ (FIG. 10 B) or treated with ganciclovir (FIG. 10 C).

REFERENCES

1. Korc M. Pancreatic cancer-associated stroma production. *Am J Surg* 2007; 194(4 Suppl):S84-6.
2. Ahmed F, Steele J C, Herbert J M, et al. Tumor stroma as a target in cancer. *Curr Cancer Drug Targets* 2008; 8(6):447-53.
3. Farrow B, Sugiyama Y, Chen A, et al. Inflammatory mechanisms contributing to pancreatic cancer development. *Ann Surg* 2004; 239(6):763-9; discussion 769-71.
4. Karnoub A E, Weinberg R A. Chemokine networks and breast cancer metastasis. *Breast Dis* 2006; 26:75-85.
5. Kiaris H, Trimis G, Papavassiliou A G. Regulation of tumor-stromal fibroblast interactions: implications in anti-cancer therapy. *Curr Med Chem* 2008; 15(29):3062-7.
6. Orimo A, Weinberg R A. Stromal fibroblasts in cancer: a novel tumor-promoting cell type. *Cell Cycle* 2006; 5(15):1597-601.
7. Fritz V, Jorgensen C. Mesenchymal stem cells: an emerging tool for cancer targeting and therapy. *Curr Stem Cell Res Ther* 2008; 3(1):32-42.
8. Zipori D. The mesenchyme in cancer therapy as a target tumor component, effector cell modality and cytokine expression vehicle. *Cancer Metastasis Rev* 2006; 25(3):459-67.
9. Karnoub A E, Dash A B, Vo A P, et al. Mesenchymal stem cells within tumour stroma promote breast cancer metastasis. *Nature* 2007; 449(7162):557-63.
10. Moller C, Stromberg T, Juremalm M, et al. Expression and function of chemokine receptors in human multiple myeloma. *Leukemia* 2003; 17(1):203-10.
11. Soria G, Ben-Baruch A. The inflammatory chemokines CCL2 and CCL5 in breast cancer. *Cancer Lett* 2008; 267(2):271-85.
12. Fischer M, Juremalm M, Olsson N, et al. Expression of CCL5/RANTES by Hodgkin and Reed-Sternberg cells and its possible role in the recruitment of mast cells into lymphomatous tissue. *Int J Cancer* 2003; 107(2):197-201.
13. Bexell D, Gunnarsson S, Tormin A, et al. Bone marrow multipotent mesenchymal stroma cells act as pericyte-like migratory vehicles in experimental gliomas. *Mol Ther* 2009; 17(1):183-90.
14. Kanehira M, Katagiri T, Shimo A, et al. Oncogenic role of MPHOSPH1, a cancer-testis antigen specific to human bladder cancer. *Cancer Res* 2007; 67(7):3276-85.
15. Von Luttichau I, Notohamiprodjo M, Wechselberger A, et al. Human adult CD34− progenitor cells functionally express the chemokine receptors CCR1, CCR4, CCR7, CXCR5, and CCR10 but not CXCR4. *Stem Cells Dev* 2005; 14(3):329-36.
16. Conrad C, Niess H, Huss R, et al. Multipotent Mesenchymal Stem Cells Acquire a Lymphendothelial Phenotype and Enhance Lymphatic Regeneration In Vivo. *Circulation* 2008.
17. Conrad C, Gupta R, Mohan H, et al. Genetically engineered stem cells for therapeutic gene delivery. *Curr Gene Ther* 2007; 7(4):249-60.
18. Kumar D, Hosse J, von Toerne C, et al. JNK MAPK pathway regulates constitutive transcription of CCL5 by human NK cells through SP1. *J Immunol* 2009; 182(2):1011-20.

19. Liyanage U K, Goedegebuure P S, Moore T T, et al. Increased prevalence of regulatory T cells (Treg) is induced by pancreas adenocarcinoma. *J Immunother* 2006; 29(4):416-24.
20. Segerer S, Banas B, Wornle M, et al. CXCR3 is involved in tubulointerstitial injury in human glomerulonephritis. *Am J Pathol* 2004; 164(2):635-49.
21. Conrad C, Gottgens B, Kinston S, et al. GATA transcription in a small rhodamine 123(low) CD34(+) subpopulation of a peripheral blood-derived CD34(−) CD105 (+) mesenchymal cell line. *Exp Hematol* 2002; 30(8):887-95.
22. Nelson P J, Kim H T, Manning W C, et al. Genomic organization and transcriptional regulation of the RANTES chemokine gene. *J Immunol* 1993; 151(5): 2601-12.
23. Werner T, Fessele S, Maier H, Nelson P J. Computer modeling of promoter organization as a tool to study transcriptional coregulation. *FASEB J* 2003; 17(10):1228-37.
24. von Luettichau I, Nelson P J, Pattison J M, et al. RANTES chemokine expression in diseased and normal human tissues. *Cytokine* 1996; 8(1):89-98.
25. Nelson P J, Pattison J M, Krensky A M. Gene expression of RANTES. *Methods Enzymol* 1997; 287:148-62.
26. Fessele S, Boehlk S, Mojaat A, et al. Molecular and in silico characterization of a promoter module and C/EBP element that mediate LPS-induced RANTES/CCL5 expression in monocytic cells. *FASEB J* 2001; 15(3):577-9.
27. Fessele S, Maier H, Zischek C, et al. Regulatory context is a crucial part of gene function. *Trends Genet.* 2002; 18(2):60-3.
28. Golumbek P T, Hamzeh F M, Jaffee E M, et al. Herpes simplex-1 virus thymidine kinase gene is unable to completely eliminate live, nonimmunogenic tumor cell vaccines. *J Immunother* 1992; 12(4):224-30.
29. Andoh A, Takaya H, Saotome T, et al. Cytokine regulation of chemokine (IL-8, MCP-1, and RANTES) gene expression in human pancreatic periacinar myofibroblasts. *Gastroenterology* 2000; 119(1):211-9.
30. Duell E J, Casella D P, Burk R D, et al. Inflammation, genetic polymorphisms in proinflammatory genes TNF-A, RANTES, and CCR5, and risk of pancreatic adenocarcinoma. *Cancer Epidemiol Biomarkers Prev* 2006; 15(4):726-31.
31. Corbett T. H., Roberts B J, Leopold W R, et al. Induction and chemotherapeutic response of two transplantable ductal adenocarcinomas of the pancreas in C57BL/6 mice. *Cancer Res* 1984; 44: 717-726
32. Morikane K, Tempero R M, Sivinski C L, et al. Organ-specific pancreatic tumor growth properties and tumor immunity. *Cancer Immunol Immunother* 1999; 47(5): 287-96.
33. Deeg H J, Klingemann H G, Philips G L, A Guide to Bone Marrow Transplantation. Springer-Verlag Berlin Heidelberg 1992.
34. Remington: The Science and Practice of Pharmacy, 20$^{th}$ Ed., p. 808, Lippincott Williams & Wilkins (2000).
35. Marfaing-Koka, A., et al., Regulation of the production of the RANTES chemokine by endothelial cells. Synergistic induction by IFN-gamma plus TNF-alpha and inhibition by IL-4 and IL-13. Journal of Immunology, 1995. 154(4): p. 1870-8.
36. Khoury, M, et al. (2007). Inflammation-inducible anti-TNF gene expression mediated by intra-articular injection of serotype 5 adeno-associated virus reduces arthritis. J Gene Med 9: 596-604.
37. Balkwill, F, Charles, K A, and Mantovani, A (2005). Smoldering and polarized inflammation in the initiation and promotion of malignant disease. *Cancer Cell* 7: 211-217.
38. Treschow, A, Unger, C, Aints, A, Felldin, U, Aschan, J, and Dilber, M S (2007). OuaSelect, a novel ouabain-resistant human marker gene that allows efficient cell selection within 48 h. *Gene Ther* 14: 1564-1572.
39. Fehse, B, et al. (2000). CD34 splice variant: an attractive marker for selection of gene-modified cells. *Mol Ther* 1: 448-456.
40. Bergoglio, V, et al. (2007). Safe selection of genetically manipulated human primary keratinocytes with very high growth potential using CD24. *Mol Ther* 15: 2186-2193.
41. Wei, Q, Croy, B A, and Etches, R J (2001). Selection of genetically modified chicken blastodermal cells by magnetic-activated cell sorting. *Poult Sci* 80: 1671-1678.
42. Niwa, H, Yamamura, K, and Miyazaki, J (1991). Efficient selection for high-expression transfectants with a novel eukaryotic vector. *Gene* 108: 193-199.
43. Zychlinski, D, et al. (2008). Physiological Promoters Reduce the Genotoxic Risk of Integrating Gene Vectors. *Mol. Ther.*
44. West, A G, Gaszner, M, and Felsenfeld, G (2002). Insulators: many functions, many mechanisms. *Genes Dev* 16: 271-288.
45. Miletic, H, et al. (2004). Selective transduction of malignant glioma by lentiviral vectors pseudotyped with lymphocytic choriomeningitis virus glycoproteins. *Hum Gene Ther* 15: 1091-1100.
46. Di Nunzio, F, Piovani, B, Cosset, F L, Mavilio, F, and Stornaiuolo, A (2007). Transduction of human hematopoietic stem cells by lentiviral vectors pseudotyped with the RD114-TR chimeric envelope glycoprotein. *Hum Gene Ther* 18: 811-820.
47. Stitz, J, et al. (2000). Lentiviral vectors pseudotyped with envelope glycoproteins derived from gibbon ape leukemia virus and murine leukemia virus 10A1. *Virology* 273: 16-20.
48. Huber, B E, Austin, E A, Richards, C A, Davis, S T, and Good, S S (1994). Metabolism of 5-fluorocytosine to 5-fluorouracil in human colorectal tumor cells transduced with the cytosine deaminase gene: significant antitumor effects when only a small percentage of tumor cells express cytosine deaminase. *Proc Natl Acad Sci USA* 91: 8302-8306.
49. Horwitz E M, Le B K, Dominici M, et al. *Clarification of the nomenclature for MSC*: the International Society for Cellular Therapy position statement. *Cytotherapy* (2005) 7:393-395.
50. Hu, W S, and Pathak, V K (2000). Design of retroviral vectors and helper cells for gene therapy. *Pharmacol Rev* 52: 493-511.
51. zsvak, Z, Ivics, Z, and Plasterk, R H (2000). Sleeping Beauty, a wide host-range transposon vector for genetic transformation in vertebrates. *J Mol Biol* 302: 93-102.
52. Wu, S C, et al. (2006). piggyBac is a flexible and highly active transposon as compared to sleeping beauty, Tol2, and Mos1 in mammalian cells. *Proc Natl Acad Sci USA* 103: 15008-15013.
53. Hanchen Li, Xueli Fan, and JeanMarie Houghton, Journal of Cellular Biochemistry 101:805-815 (2007).

54. Balkwill, F., K. A. Charles, et al. (2005). "Smoldering and polarized inflammation in the initiation and promotion of malignant disease." *Cancer Cell* 7(3): 211-7.

55. Inman, G. J. and C. S. Hill (2002). "Stoichiometry of active smad-transcription factor complexes on DNA." *Journal of Biological Chemistry* 277(52): 51008-16.

The invention claimed is:

1. A method for treating a subject afflicted with a tumor comprising introducing into the subject's bloodstream a therapeutically effective number of genetically modified mesenchymal stem cells, wherein each genetically modified mesenchymal stem cell contains an exogenous nucleic acid comprising (i) a cytotoxic protein-encoding region operably linked to (ii) a RANTES promoter.

2. The method of claim 1, wherein the subject is human.

3. The method of claim 1, wherein the tumor is metastatic.

4. The method of claim 1, wherein the tumor is vascularized.

5. The method of claim 1, wherein the tumor is not vascularized.

6. The method of claim 1, wherein the genetically modified mesenchymal stem cells are CD34$^-$ stem cells.

7. The method of claim 1, wherein the genetically modified mesenchymal stem cells are allogenic with respect to the subject.

8. The method of claim 1, wherein the genetically modified mesenchymal stem cells are autologous with respect to the subject.

9. The method of claim 1, wherein the tumor's stromal tissue comprises fibroblast-like cells.

10. The method of claim 1, wherein the introduction of the genetically modified mesenchymal stem cells is not preceded, accompanied or followed by myeloablation.

11. The method of claim 1, wherein the tumor is selected from the group consisting of a prostate tumor, a breast tumor, a pancreatic tumor, a squamous cell carcinoma, a breast tumor, a melanoma, a basal cell carcinoma, a hepatocellular carcinoma, testicular cancer, a neuroblastoma, a glioma or a malignant astrocytic tumor, a colorectal tumor, an endometrial carcinoma, a lung carcinoma, an ovarian tumor, a cervical tumor, an osteosarcoma, a rhabdo/leiomyosarcoma, a synovial sarcoma, an angiosarcoma, an Ewing sarcoma/PNET and a malignant lymphoma.

12. The method of claim 1, wherein the tumor is a pancreatic tumor.

13. The method of claim 1, wherein the cytotoxic protein is Herpes simplex viral thymidine kinase, and the subject is treated with ganciclovir in a manner permitting the Herpes simplex viral thymidine kinase to render the ganciclovir cytotoxic.

14. The method of claim 1, wherein the therapeutically effective number of genetically modified mesenchymal stem cells is from about $1 \times 10^5$ to about $1 \times 10^9$ cells/kg body weight.

15. The method of claim 1, wherein the therapeutically effective number of genetically modified mesenchymal stem cells is from about $1 \times 10^6$ to about $1 \times 10^8$ cells/kg body weight.

16. The method of claim 15, wherein the therapeutically effective number of genetically modified mesenchymal stem cells is from about $5 \times 10^6$ to about $2 \times 10^7$ cells/kg body weight.

17. A genetically modified mesenchymal stem cell comprising an exogenous nucleic acid comprising (i) a cytotoxic protein-encoding region operably linked to (ii) a RANTES promoter.

18. The stem cell of claim 17, wherein the stem cell is a human stem cell.

19. The stem cell of claim 17, wherein the stem cell is a CD34$^-$ stem cell.

20. The stem cell of claim 17, further comprising a (iii) selection marker gene operably linked to (iv) a constitutive promoter or promoter/enhancer combination.

21. The stem cell of claim 20, wherein the selection marker gene comprises an antibiotic resistance gene or a gene encoding a surface marker protein.

22. The stem cell of claim 20, further comprising an (v) insulator sequence located between the cytotoxic protein-encoding region and a surface marker gene.

23. The stem cell of claim 17, wherein the cytotoxic protein-encoding region operably linked to the RANTES promoter is integrated into the stem cell genome.

24. The stem cell of claim 20, wherein the selection marker gene operably linked to the constitutive promoter or promoter/enhancer combination is integrated into the stem cell genome.

25. The stem cell of claim 20, wherein the cytotoxic protein-encoding region operably linked to the RANTES promoter and the selection marker gene operably linked to the constitutive promoter or promoter/enhancer combination are a part of a proviral sequence integrated into the stem cell genome.

26. The stem cell of claim 25, wherein the proviral sequence is a lentiviral, alpha-retroviral or gamma-retroviral sequence.

27. The stem cell of claim 17, wherein the cytotoxic protein is Herpes simplex viral thymidine kinase or cytosine deaminase.

28. An isolated genetically modified human CD34$^-$ stem cell comprising an exogenous nucleic acid comprising (i) a Herpes simplex viral thymidine kinase-encoding region operably linked to (ii) a RANTES promoter.

29. The method of claim 11, wherein the glioma or malignant astrocyte is a glioblastoma multiforme.

30. The method according to claim 1, wherein the therapeutically effective number of genetically modified mesenchymal stem cells is introduced into the subject's bloodstream via intravenous injection.

* * * * *

UNITED STATES PATENT AND TRADEMARK OFFICE
CERTIFICATE OF CORRECTION

PATENT NO. : 9,434,925 B2
APPLICATION NO. : 13/264084
DATED : September 6, 2016
INVENTOR(S) : Peter J. Nelson Page 1 of 1

It is certified that error appears in the above-identified patent and that said Letters Patent is hereby corrected as shown below:

In the Specification

In column 1 at line 34, change "endocrins" to --endocrine--.

In column 1 at line 40, after "fibroblasts" insert --.--.

In column 3 at lines 61-62, change "incapsidation" to --encapsidation--.

In column 6 at line 48, change "glioblastma" to --glioblastoma--.

In column 7 at line 33, change "glioblastma" to --glioblastoma--.

In column 9 at line 12 (approx.), after ")" insert --.--.

In column 9 at lines 54-55, change "Lipofectamin)" to --Lipofectamine)--.

In column 10 at line 42, after "promoters" insert --.--.

In column 17 at line 10, change "HSV Tk" to --HSV tk--.

In the Claims

In column 22 at line 45 (approx.), after "isolated" insert --,--.

Signed and Sealed this
Twenty-seventh Day of December, 2016

Michelle K. Lee
*Director of the United States Patent and Trademark Office*